US007838544B2

(12) United States Patent
Li et al.

(10) Patent No.: US 7,838,544 B2
(45) Date of Patent: Nov. 23, 2010

(54) HETEROCYCLIC INHIBITORS OF 11-β HYDROXYL STEROID DEHYDROGENASE TYPE 1 AND METHODS OF USING THE SAME

(75) Inventors: Yun-Long Li, Chadds Ford, PA (US); Jincong Zhuo, Boothwyn, PA (US); Wenqing Yao, Kennett Square, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 11/803,808

(22) Filed: May 16, 2007

(65) Prior Publication Data

US 2007/0270424 A1 Nov. 22, 2007

Related U.S. Application Data

(60) Provisional application No. 60/801,326, filed on May 17, 2006, provisional application No. 60/808,703, filed on May 26, 2006.

(51) Int. Cl.
*A61K 31/4196* (2006.01)
*C07D 249/08* (2006.01)
(52) U.S. Cl. ..................... 514/383; 548/262.2
(58) Field of Classification Search .............. 514/235.5, 514/326, 383; 544/139, 140; 546/210, 209; 548/262.2
See application file for complete search history.

(56) References Cited

U.S. PATENT DOCUMENTS

| | | | |
|---|---|---|---|
| 3,666,860 A | 5/1972 | Berkelhammer et al. |
| 3,770,748 A | 11/1973 | Borck et al. |
| 3,933,829 A | 1/1976 | Archibald et al. |
| 4,001,422 A | 1/1977 | Danilewicz et al. |
| 4,013,445 A | 3/1977 | Bellus et al. |
| 4,076,819 A | 2/1978 | Maffrand |
| 4,439,606 A | 3/1984 | Du et al. |
| 5,076,961 A | 12/1991 | Nakamura et al. |
| 5,442,064 A | 8/1995 | Pieper et al. |
| 5,614,534 A | 3/1997 | Binet et al. |
| 5,633,247 A | 5/1997 | Baldwin et al. |
| 5,668,138 A | 9/1997 | Baziard-Mouysset et al. |
| 5,852,029 A | 12/1998 | Fisher et al. |
| 5,981,754 A | 11/1999 | Badone et al. |
| 6,547,958 B1 | 4/2003 | Elomari et al. |
| 2003/0229119 A1 | 12/2003 | Kym et al. |
| 2005/0020645 A1 | 1/2005 | Ohta et al. |
| 2005/0080078 A1 | 4/2005 | Aquila et al. |
| 2005/0282858 A1 | 12/2005 | Yao et al. |
| 2005/0288317 A1 | 12/2005 | Yao et al. |
| 2005/0288329 A1 | 12/2005 | Yao et al. |
| 2005/0288338 A1 | 12/2005 | Yao et al. |
| 2006/0004049 A1 | 1/2006 | Yao et al. |
| 2006/0009471 A1 | 1/2006 | Yao et al. |
| 2006/0009491 A1 | 1/2006 | Yao et al. |
| 2006/0019977 A1 | 1/2006 | Habashita et al. |
| 2006/0106045 A1 | 5/2006 | Hughes et al. |
| 2006/0116382 A1 | 6/2006 | Yao et al. |
| 2006/0122197 A1 | 6/2006 | Yao et al. |
| 2006/0122210 A1 | 6/2006 | Yao et al. |
| 2006/0149070 A1 | 7/2006 | Rohde et al. |
| 2006/0199816 A1 | 9/2006 | Gillespie et al. |
| 2007/0066584 A1 | 3/2007 | Yao et al. |
| 2007/0129345 A1 | 6/2007 | Zhuo et al. |
| 2007/0179142 A1 | 8/2007 | Yao et al. |
| 2007/0197506 A1 | 8/2007 | Yao et al. |
| 2007/0197530 A1 | 8/2007 | Li et al. |
| 2007/0208001 A1 | 9/2007 | Zhuo et al. |
| 2007/0213311 A1 | 9/2007 | Li et al. |
| 2007/0275990 A1 | 11/2007 | Ohmoto et al. |
| 2007/0293529 A1 | 12/2007 | Li et al. |
| 2008/0255154 A1 | 10/2008 | Yao et al. |
| 2008/0318991 A1 | 12/2008 | Yao et al. |

FOREIGN PATENT DOCUMENTS

| | | |
|---|---|---|
| DE | 2623567 | 12/1976 |
| DE | 136963 | 8/1979 |
| EP | 1683797 | 7/2006 |
| JP | 4334357 | 11/1992 |
| WO | WO 03037847 | 5/2003 |
| WO | WO 03/053915 | 7/2003 |
| WO | WO 03/065983 | 8/2003 |
| WO | WO 2004/056745 | 7/2004 |
| WO | WO 2004/056789 | 7/2004 |
| WO | WO 2004/058253 | 7/2004 |
| WO | WO 2004065351 | 8/2004 |
| WO | WO 2004/082687 | 9/2004 |
| WO | WO 2004089470 | 10/2004 |

(Continued)

OTHER PUBLICATIONS

Alberts et al. Endocrinology (2003) 144: 4755-4762.

(Continued)

*Primary Examiner*—Kamal A Saeed
*Assistant Examiner*—Kristin Bianchi
(74) *Attorney, Agent, or Firm*—Fish & Richardson P.C.

(57) ABSTRACT

The present invention relates to inhibitors of 11-β hydroxyl steroid dehydrogenase type 1 and pharmaceutical compositions thereof. The compounds of the invention can be useful in the treatment of various diseases associated with expression or activity of 11-β hydroxyl steroid dehydrogenase type 1.

45 Claims, No Drawings

FOREIGN PATENT DOCUMENTS

| WO | WO 2004089896 | 10/2004 |
| --- | --- | --- |
| WO | WO 2004/106294 | 12/2004 |
| WO | WO 2005/044192 | 5/2005 |
| WO | WO 2005047286 | 5/2005 |
| WO | WO 2005060963 | 7/2005 |
| WO | WO 2005063745 | 7/2005 |
| WO | WO 2005/087764 * | 9/2005 |
| WO | WO 2005/095350 | 10/2005 |
| WO | WO 2005/110992 | 11/2005 |
| WO | WO 2005108359 | 11/2005 |
| WO | WO 2006002350 | 1/2006 |
| WO | WO 2006/012227 | 2/2006 |
| WO | WO 2006/020598 | 2/2006 |
| WO | WO 2006012226 | 2/2006 |
| WO | WO 2006/047196 | 5/2006 |
| WO | WO 2006/080533 | 8/2006 |
| WO | WO 2006/130986 | 12/2006 |

OTHER PUBLICATIONS

Albiston et al. (1994) Mol. Cell. Endocrin. 105: R11-R17.
Barf et al. (2002) J. Med. Chem. 45: 3813-3815.
Bellows et al. (1998) Bone 23: 119-125.
Ben el al., "Synthesis of Opticaly Active α-Amino Esters via Dynamic Kinetic Resolution: A Mechanistic Study," J. Org. Chem. 64: 7700-7706 (1999).
Bhargava et al., (2001), Endo 142: 1587-1594.
Billaudel and Sutter (1979) Horm. Metab. Res. 11: 555-560.
Bioreversible Carriers in Drug Design, ed. Edward B. Roche, American Pharmaceutical Association and Pergamon Press, 1987.
Blum, et al., (2003) Prog. Nucl. Acid Res. Mol. Biol. 75:173-216.
Bujalska et al. (1997) Lancet 349: 1210-1213.
Buzas, A. et al., Chimica Therapeutica, The European Journal of Medicinal Chemistry,7 (5), pp. 361-426, 1972.
Canalis (1996) J. Clin. Endocrinol. Metab. 81: 3441-3447.
Conn, (1955), J. Lab. Clin. Med. 45: 6-17.
Cooper et al. (2000) Bone 27: 375-381.
Database CAPLUS on STN (Columbus, OH, USA) No. 108:131815, Preparation and testing of 17-amino-1,3-dihydro-2H-imidazo[4,5-b]quinolin-2-ones as phosphodiesterase and bloodplatelet aggregation inhibitors', abstract, Meanwell, et al. (1988) see RN 113288-90-7.
Database CAPLUS on STN (Columbus, OH, USA) No. 118:255342, {re[artopm pf M-heterpcuc:u;carbpmu;a,omp acids and analogs as prolylendopeptidase inhibotors' abstract, Hosoda et al. (1993) see RN 147635-61-8.
Database CAPLUS on STN (Columbus, OH, USA) No. 126:317635, "Alpha-amino acids derived from ornithine as building blocks for peptide synthesis" abstract, Gescrinier et al. j. Pep. Res. 49(2):183-189 (1997).
Database CAPLUS on STN (Columbus, OH, USA) No. 143:78479, "Preparation of amino acid derivatives as novel M3 muscarinic acetylcholine receptor antagonists" abstract, Busch et al. (2005), see RN 902149-23-9 and 854750-92-8.
Davani et al. (2000) J. Biol. Chem. 275: 34841-34844.
Draper et al. (2003) Nat. Genet. 34: 434-439.
Edwards et al. (1988) Lancet 2: 986-989.
Engeli, et al., (2004) Obes. Res. 12: 9-17.
Funder et al. (1988), Science 242: 583-585.
Greene, et al., Protective Groups in Organic Synthesis, 2d. Ed., Wiley & Sons, 1991.
Gu et al., "Discovery of 4-heteroarylbicyclo[2.2.2]octyltriazoles as potent and selective inhibitors of 11 β-HSDI : Novel therapeutic agents for the treatment of metabolic syndrome," Bioorg. Med Chem. Lett., 15:5266-5269 (2005).
Hermanowski-Vosatka et al. (2005) J. Exp. Med. 202: 517-527.
Irikura, Tsutomu and Kasuga, Kazunori, "New Antiulcer Agents. Syntheases and biological Activities of 1-Acyl-2, -3-, and -4-Substituted Benzamidopiperidine",Journal of Medicinal Chemistry, 14 (4), pp. 357-361, 1971.

Jausons-Loffreda et al. J. Biolumin and Chemilumin, 9:217-221 (1994).
Journal of Pharmaceutical Science, 66, 2 (1977).
Kotelevstev et al. (1997) Proc. Natl. Acad. Sci. 94: 14924-14929.
Kurukulasuriya , et al., (2003) Curr. Med. Chem. 10: 123-53.
Leonardi et al., "Synthesis, Pharmacological Evaluation, and Structure—Activity Relationship and Quantitative Structure—Activity Relationship Studies on Novel Derivatives of 2,4-Diamitto-6,7-dimethoxyquinazoline $\alpha_1$-Adrenoceptor Antagonists," J. Med. Chem., 42:427-437 (1999).
Lindsay et al. (2003) J. Clin. Endocrinol. Metab. 88: 2738-2744.
Livingstone et al. (2000) Endocrinology 131: 560-563.
Low et al. (1994) J. Mol. Endocrin. 13: 167-174.
Lupien et al. (1998) Nat. Neurosci. 1: 69-73.
Mallams et al., "Inhibitors of Farnesyl Protein Transferase, 4-Amido, 4-Carbamoyl, and 4-Carboxamido Derivatives of 1-(8-Chloro-6,11-dihydro-5H-benzo[5,6]-cyclohepta[1,2-b]pyridin-11-yl)piperazine and 1-(3-Bromo-8-chloro-6,11-dihydro-5H-benzo[5,6]cyclohepta[1,2-b]pyridin-11-yl)piperazine," J. Med. Chem., 41:877-893 (1998).
Masuzaki et al. (2001) Science 294: 2166-2170.
Masuzaki et al. (2003) J. Clinical Invest. 112: 83-90.
Masuzaki, et al., (2003) Curr. Drug Targets Immune Endocr. Metabol. Disord. 3: 255-62.
Matsumoto et al., "Direkte Aminolyse von nicht aktivierten Estern bei hohm Druck," Angew. Chem. 98: 569-570 (1986).
Matsuzawa et al. (1999) Ann. N.Y. Acad. Sci. 892: 146-154.
McEwen and Sapolsky (1995) Curr. Opin. Neurobiol. 5: 205-216.
Miller and Chrousos (2001) Endocrinology and Metabolism, eds. Felig and Frohman (McGraw-Hill, New York), 4th Ed.: 387-524.
Moeller et al., "Anodic Amide Oxidations in the Presence of Electron-Rich Phenyl Rings: Evidence for an Intramolecular Electron-Transfer Mechanism," J. Org. Chem., 56:1058-1067 (1991).
Morton et at. (2001) J. Biol. Chem. 576: 41293-41300.
Morton et al. (2004) Diabetes 53: 931-938.
Moya et al., "Synthesis and Biological Evaluation of New Analogies of the Active Fungal Metabolites N-(2-Methyl-3-oxodecanoyl)-2-pyrroline and N-(2-Methyl-3-oxodec-8-enoyl)-2-pyrroline," J. Agric. Food Chem., 47: 3866-3871 (1999).
Nojima, M. et al., Spiro Compounds Formation by the reaction of Cycloalkene wit Friedel-Crafts Catalyst. I. Reaction of Cyclohexene with Aluminum Chloride. The Rearrangement of Cyclohexylcyclohexene, Journal of Organic Chemistry, 31 (12), pp. 3966-3969, 1966.
Ogawa et al. (1992) J. Clin. Invest. 90: 497-504.
Ogura, K. et al., "[1,4] Addition of (Methylthio p-Tolyl Sulfone to α,β-Unaturated Carbonyl Compounds", Journal of Organic Chemistry, 51, pp. 508-512, 1986.
Pitt et al., New England J. Med. (1999), 341: 709-719.
Pitt et al., New England J. Med, (2003), 348: 1309-1321.
Rajan et al. (1996) J. Neurosci. 16: 65-70.
Rask et al. (2001) J. Clin. Endocrinol. Metab. 86: 1418-1421.
Rauz et al. (2001) Invest. Ophthalmol. Vis. Sci. 42: 2037-2042.
Reaven (1993) Ann. Rev. Med. 44: 121-131.
Remington's Pharmaceutical Sciences, 17th ed., Mack Publishing Company, Easton, Pa., 1985, p. 1418.
Sandeep et al. (2004) Proc. Natl. Acad. Sci. 101: 6734-6739.
Schelsinger et al., "N-Substituted-Amides," J. Am. Chem. Soc., 78: 6123-6127 (1956).
Stokes et al. (2000) Invest. Ophthalmol. Vis. Sci. 41: 1629-1683.
T. Higuchi and V. Stella, "Pro-drugs as Novel Delivery Systems," vol. 14 of the A.C.S. Symposium Series, and in Bioreversible Carriers in Drug Design, ed. Edward B. Roche, American Pharmaceutical Association and Pergamon Press, 1987.
Wajchenberg, B.L. (2000) Endocrine Reviews 21: 697-738.
Wake et al. (2003) J. Clin. Endocrinol. Metab. 88: 3983-3988.
Walker et al. (1979) Hypertension 1: 287-291.
Wheatley et al., "Basic Ethers Derived from β-Hydroxyphenethylamines," J. Org. Chem., 23: 1360-1363 (1958).
Wilson et al. (1998) Proc. Natl. Acad. Sci. 95: 10200-10205.
Wojcik et al., "Catalytic Hydrogenation of Amides to Amines," J. Am. Chem. Soc., 56:2419-2424 (1934).

Yokoyama et al., "The First Effective Syntheses of Cyanoflurormethylated Amides, Thioamides, and Phosphorus Compunds Using 2-Cyano-2-fluoro-2-phenylacetonitrile and ET$_3$GeNa," *Synthesis*, 8: 1319-1324 (1999).

International Search Report for PCT/US2007/063050, dated Jun. 20, 2007.

International Search Report for PCT/US2007/063055, dated Oct. 8, 2007.

Gu et al., "Discovery of 4-heteroarylbicyclo[2.2.2]octyltriazoles as potent and selective inhibitors of 11β-HSD1: Novel therapeutic agents for the treatment of metabolic syndrome," *Bioorg. Med. Chem. Lett.*, 15:5266-5269 (2005).

Huber, "11βHSD1 Inhibitors for Type 2 Diabetes: A Systematic Development Strategy to Assess Pharmacodynamic Activity and Obtain Proof-of-Concept in Man," IBC's 5th Annual Targeting Metabolic Disorders Conference, Feb. 26-27, 2007.

Li et al. Syntheses and SAR of piperidin-3-yl ureas as potent and selective 11-HSD-1 inhibitors, MEDI 54 Abstract of Presentation at the 233rd ACS National Meeting, Chicago, IL, Mar. 25-29, 2007.

Li et al. Syntheses and SAR of Piperidin-3-yl Ureas as Potent and Selective 11-HSD-1 inhibitors, Presentation at the 233rd ACS National Meeting, Chicago, IL, Mar. 25-29, 2007.

Yao, et al. Discovery of potent and selective 11-HSD-1 Inhibitors, MEDI 228 Abstract of Presentation at the 233rd ACS National Meeting, Chicago, IL, Mar. 25-29, 2007.

Yao, Discovery of Potent and Orally Active Inhibitors of 11-Hydroxysteroid Dehydrogenase I, presentation at the 233rd ACS National Meeting, Chicago, IL, Mar. 27, 2007.

Yao et al., "Preparation of cycloalkylcarbonylammes and heteroeyeloalkylcarbonylammes as 11 hydroxysteroid dehydrogenase type I inhibitors and mineraloeorticoid receptor antagonist and their use as pharmaceutical", Caplus English Abstract DN 144.6815, Nov. 2005.

Yeh et al., "Discovery of orally active butyrolactam 11β-HSD1 inhibitors," *Bioorg. Med. Chem. Lett.*, 16:5555-5560 (2006).

Yeh et al., "Synthesis and biological evaluation of heterocycle containing adamantine 11β-HSD1 inhibitors," *Bioorg. Med. Chem. Lett.*, 16:5414-5419 (2006).

Zhuo. et al. Discovery and synthesis of nipecotic amide as novel, potent and selective 11-HSD-1- inhibitors MEDI 48 Abstract, 233rd ACS National Meeting, Chicago, IL, Mar. 25-29, 2007.

Zhuo et al. Discovery of Nipecotic Amides as Novel, Potent and Selective 11 HSD1 Inhibitors, poster at the 233rd ACS National Meeting, Chicago, IL, Mar. 25-29, 2007.

Database CAPLUS, on STN (Columbus, OH, USA), 1987:598246, No.107:198246, "Pyperazine derivatives. XVII. Synthesis and Tuberculostatic Activity of Pyrazinyl-1, 3, 4-oxadiazole Derivatives", abstract, Pancechowska-Ksepko et al., 1986, see RN 109538-74-1, XP-002464725,.

Database CAPLUS, on STN (Columbus, OH, USA) 1985:78786, No. 102:78786, 102:12353a,12356a, "Some Reactions of 5-(3- or 4-pyridyl) -1,3, 4-oxidiazoles with Amines and Hydrazines", abstract, Zayed, S.A. et al., et al., 1984, see RN 94696-15-8, 94696-16-91. XP-002464726.

Database CAPLUS, on STN (Columbus, OH, USA) 2006:768409, No. 145:211047, Preparation of 3-amino-1,2,4-triazole derivatives as 11.beta.-hydroxysteroid dehydrogenase type 1 inhibitors, abstract, Manabu, I. et al, see RN 904321-63-7, 904321-80-8, 904321-81-9. XP-002464555, 2006.

Scott, F. L. et al., "Synthesis and Reactions of Trihalogeno-Diazabutadienes—New Versatile Synthetic Intermediates", *Tetrahedron Letters*, 47, pp. 4079-4082, 1970.

International Search Report for PCT/US2007/0669033, dated Jan. 24, 2008.

\* cited by examiner

US 7,838,544 B2

HETEROCYCLIC INHIBITORS OF 11-β HYDROXYL STEROID DEHYDROGENASE TYPE 1 AND METHODS OF USING THE SAME

CROSS REFERENCE TO RELATED APPLICATIONS

This application claims the benefit of U.S. Provisional App. Nos. 60/801,326, filed May 17, 2006 and 60/808,703, filed May 26, 2006, the disclosures of each of which are incorporated herein by reference in their entireties.

TECHNICAL FIELD

The present invention relates to modulators of 11-β hydroxyl steroid dehydrogenase type 1 (11βHSD1), compositions thereof and methods of using the same.

BACKGROUND

Glucocorticoids are steroid hormones that regulate fat metabolism, function and distribution. In vertebrates, glucocorticoids also have profound and diverse physiological effects on development, neurobiology, inflammation, blood pressure, metabolism and programmed cell death. In humans, the primary endogenously-produced glucocorticoid is cortisol. Cortisol is synthesized in the zona fasciculate of the adrenal cortex under the control of a short-term neuroendocrine feedback circuit called the hypothalamic-pituitary-adrenal (HPA) axis. Adrenal production of cortisol proceeds under the control of adrenocorticotrophic hormone (ACTH), a factor produced and secreted by the anterior pituitary. Production of ACTH in the anterior pituitary is itself highly regulated, driven by corticotropin releasing hormone (CRH) produced by the paraventricular nucleus of the hypothalamus. The HPA axis maintains circulating cortisol concentrations within restricted limits, with forward drive at the diurnal maximum or during periods of stress, and is rapidly attenuated by a negative feedback loop resulting from the ability of cortisol to suppress ACTH production in the anterior pituitary and CRH production in the hypothalamus.

Aldosterone is another hormone produced by the adrenal cortex; aldosterone regulates sodium and potassium homeostasis. Fifty years ago, a role for aldosterone excess in human disease was reported in a description of the syndrome of primary aldosteronism (Conn, (1955), *J. Lab. Clin. Med.* 45: 6-17). It is now clear that elevated levels of aldosterone are associated with deleterious effects on the heart and kidneys, and are a major contributing factor to morbidity and mortality in both heart failure and hypertension.

Two members of the nuclear hormone receptor superfamily, glucocorticoid receptor (GR) and mineralocorticoid receptor (MR), mediate cortisol function in vivo, while the primary intracellular receptor for aldosterone is the MR. These receptors are also referred to as 'ligand-dependent transcription factors,' because their functionality is dependent on the receptor being bound to its ligand (for example, cortisol); upon ligand-binding these receptors directly modulate transcription via DNA-binding zinc finger domains and transcriptional activation domains.

Historically, the major determinants of glucocorticoid action were attributed to three primary factors: 1) circulating levels of glucocorticoid (driven primarily by the HPA axis), 2) protein binding of glucocorticoids in circulation, and 3) intracellular receptor density inside target tissues. Recently, a fourth determinant of glucocorticoid function was identified: tissue-specific pre-receptor metabolism by glucocorticoid-activating and -inactivating enzymes. These 11-beta-hydroxysteroid dehydrogenase (11-β-HSD) enzymes act as pre-receptor control enzymes that modulate activation of the GR and MR by regulation of glucocorticoid hormones. To date, two distinct isozymes of 11-beta-HSD have been cloned and characterized: 11βHSD1 (also known as 11-beta-HSD type 1, 11betaHSD1, HSD11B1, HDL, and HSD11L) and 11βHSD2. 11βHSD1 and 11βHSD2 catalyze the interconversion of hormonally active cortisol (corticosterone in rodents) and inactive cortisone (11-dehydrocorticosterone in rodents). 11βHSD1 is widely distributed in rat and human tissues; expression of the enzyme and corresponding mRNA have been detected in lung, testis, and most abundantly in liver and adipose tissue. 11βHSD1 catalyzes both 11-beta-dehydrogenation and the reverse 11-oxoreduction reaction, although 11βHSD1 acts predominantly as a NADPH-dependent oxoreductase in intact cells and tissues, catalyzing the activation of cortisol from inert cortisone (Low et al. (1994) *J. Mol. Endocrin.* 13: 167-174) and has been reported to regulate glucocorticoid access to the GR. Conversely, 11βHSD2 expression is found mainly in mineralocorticoid target tissues such as kidney, placenta, colon and salivary gland, acts as an NAD-dependent dehydrogenase catalyzing the inactivation of cortisol to cortisone (Albiston et al. (1994) *Mol. Cell. Endocrin.* 105: R11-R17), and has been found to protect the MR from glucocorticoid excess, such as high levels of receptor-active cortisol (Blum, et al., (2003) *Prog. Nucl. Acid Res. Mol. Biol.* 75:173-216).

In vitro, the MR binds cortisol and aldosterone with equal affinity. The tissue specificity of aldosterone activity, however, is conferred by the expression of 11βHSD2 (Funder et al. (1988), *Science* 242: 583-585). The inactivation of cortisol to cortisone by 11βHSD2 at the site of the MR enables aldosterone to bind to this receptor in vivo. The binding of aldosterone to the MR results in dissociation of the ligand-activated MR from a multiprotein complex containing chaperone proteins, translocation of the MR into the nucleus, and its binding to hormone response elements in regulatory regions of target gene promoters. Within the distal nephron of the kidney, induction of serum and glucocorticoid inducible kinase-1 (sgk-1) expression leads to the absorption of Na$^+$ ions and water through the epithelial sodium channel, as well as potassium excretion with subsequent volume expansion and hypertension (Bhargava et al., (2001), *Endo* 142: 1587-1594).

In humans, elevated aldosterone concentrations are associated with endothelial dysfunction, myocardial infarction, left ventricular atrophy, and death. In attempts to modulate these ill effects, multiple intervention strategies have been adopted to control aldosterone overactivity and attenuate the resultant hypertension and its associated cardiovascular consequences. Inhibition of angiotensin-converting enzyme (ACE) and blockade of the angiotensin type 1 receptor (AT1R) are two strategies that directly impact the rennin-angiotensin-aldosterone system (RAAS). However, although ACE inhibition and AT1R antagonism initially reduce aldosterone concentrations, circulating concentrations of this hormone return to baseline levels with chronic therapy (known as 'aldosterone escape'). Importantly, co-administration of the MR antagonist Spironolactone or Eplerenone directly blocks the deleterious effects of this escape mechanism and dramatically reduces patient mortality (Pitt et al., *New England J. Med.* (1999), 341: 709-719; Pitt et al., *New England J. Med.* (2003), 348: 1309-1321). Therefore, MR antagonism may be an important treatment strategy for many patients with hypertension and cardiovascular disease, particularly those hypertensive patients at risk for target-organ damage.

Mutations in either of the genes encoding the 11-beta-HSD enzymes are associated with human pathology. For example, 11βHSD2 is expressed in aldosterone-sensitive tissues such as the distal nephron, salivary gland, and colonic mucosa where its cortisol dehydrogenase activity serves to protect the intrinsically non-selective MR from illicit occupation by cortisol (Edwards et al. (1988) Lancet 2: 986-989). Individuals with mutations in 11βHSD2 are deficient in this cortisol-inactivation activity and, as a result, present with a syndrome of apparent mineralocorticoid excess (also referred to as 'SAME') characterized by hypertension, hypokalemia, and sodium retention (Wilson et al. (1998) Proc. Natl. Acad. Sci. 95: 10200-10205). Likewise, mutations in 11βHSD1, a primary regulator of tissue-specific glucocorticoid bioavailability, and in the gene encoding a co-localized NADPH-generating enzyme, hexose 6-phosphate dehydrogenase (H6PD), can result in cortisone reductase deficiency (CRD), in which activation of cortisone to cortisol does not occur, resulting in adrenocorticotropin-mediated androgen excess. CRD patients excrete virtually all glucocorticoids as cortisone metabolites (tetrahydrocortisone) with low or absent cortisol metabolites (tetrahydrocortisols). When challenged with oral cortisone, CRD patients exhibit abnormally low plasma cortisol concentrations. These individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

The importance of the HPA axis in controlling glucocorticoid excursions is evident from the fact that disruption of homeostasis in the HPA axis by either excess or deficient secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Patients with Cushing's syndrome (a rare disease characterized by systemic glucocorticoid excess originating from the adrenal or pituitary tumors) or receiving glucocorticoid therapy develop reversible visceral fat obesity. Interestingly, the phenotype of Cushing's syndrome patients closely resembles that of Reaven's metabolic syndrome (also known as Syndrome X or insulin resistance syndrome) the symptoms of which include visceral obesity, glucose intolerance, insulin resistance, hypertension, type 2 diabetes and hyperlipidemia (Reaven (1993) Ann. Rev. Med. 44: 121-131). However, the role of glucocorticoids in prevalent forms of human obesity has remained obscure because circulating glucocorticoid concentrations are not elevated in the majority of metabolic syndrome patients. In fact, glucocorticoid action on target tissue depends not only on circulating levels but also on intracellular concentration, locally enhanced action of glucocorticoids in adipose tissue and skeletal muscle has been demonstrated in metabolic syndrome. Evidence has accumulated that enzyme activity of 11βHSD1, which regenerates active glucocorticoids from inactive forms and plays a central role in regulating intracellular glucocorticoid concentration, is commonly elevated in fat depots from obese individuals. This suggests a role for local glucocorticoid reactivation in obesity and metabolic syndrome.

Given the ability of 11βHSD1 to regenerate cortisol from inert circulating cortisone, considerable attention has been given to its role in the amplification of glucocorticoid function. 11βHSD1 is expressed in many key GR-rich tissues, including tissues of considerable metabolic importance such as liver, adipose, and skeletal muscle, and, as such, has been postulated to aid in the tissue-specific potentiation of glucocorticoid-mediated antagonism of insulin function. Considering a) the phenotypic similarity between glucocorticoid excess (Cushing's syndrome) and the metabolic syndrome with normal circulating glucocorticoids in the latter, as well as b) the ability of 11βHSD1 to generate active cortisol from inactive cortisone in a tissue-specific manner, it has been suggested that central obesity and the associated metabolic complications in syndrome X result from increased activity of 11βHSD1 within adipose tissue, resulting in 'Cushing's disease of the omentum' (Bujalska et al. (1997) Lancet 349: 1210-1213). Indeed, 11βHSD1 has been shown to be upregulated in adipose tissue of obese rodents and humans (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Additional support for this notion has come from studies in mouse transgenic models. Adipose-specific overexpression of 11βHSD1 under the control of the aP2 promoter in mouse produces a phenotype remarkably reminiscent of human metabolic syndrome (Masuzaki et al. (2001) Science 294: 2166-2170; Masuzaki et al. (2003) J. Clinical Invest. 112: 83-90). Importantly, this phenotype occurs without an increase in total circulating corticosterone, but rather is driven by a local production of corticosterone within the adipose depots. The increased activity of 11βHSD1 in these mice (2-3 fold) is very similar to that observed in human obesity (Rask et al. (2001) J. Clin. Endocrinol. Metab. 86: 1418-1421). This suggests that local 11βHSD1-mediated conversion of inert glucocorticoid to active glucocorticoid can have profound influences whole body insulin sensitivity.

Based on this data, it would be predicted that the loss of 11βHSD1 would lead to an increase in insulin sensitivity and glucose tolerance due to a tissue-specific deficiency in active glucocorticoid levels. This is, in fact, the case as shown in studies with 11βHSD1-deficient mice produced by homologous recombination (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). These mice are completely devoid of 11-keto reductase activity, confirming that 11βHSD1 encodes the only activity capable of generating active corticosterone from inert 11-dehydrocorticosterone. 11βHSD1-deficient mice are resistant to diet- and stress-induced hyperglycemia, exhibit attenuated induction of hepatic gluconeogenic enzymes (PEPCK, G6P), show increased insulin sensitivity within adipose, and have an improved lipid profile (decreased triglycerides and increased cardio-protective HDL). Additionally, these animals show resistance to high fat diet-induced obesity. Further, adipose-tissue overexpression of the 11-beta dehydrogenase enzyme, 11bHSD2, which inactivates intracellular corticosterone to 11-dehydrocorticosterone, similarly attenuates weight gain on high fat diet, improves glucose tolerance, and heightens insulin sensitivity. Taken together, these transgenic mouse studies confirm a role for local reactivation of glucocorticoids in controlling hepatic and peripheral insulin sensitivity, and suggest that inhibition of 11βHSD1 activity may prove beneficial in treating a number of glucocorticoid-related disorders, including obesity, insulin resistance, hyperglycemia, and hyperlipidemia.

Data in support of this hypothesis has been published. Recently, it was reported that 11βHSD1 plays a role in the pathogenesis of central obesity and the appearance of the metabolic syndrome in humans. Increased expression of the 11βHSD1 gene is associated with metabolic abnormalities in obese women and that increased expression of this gene is suspected to contribute to the increased local conversion of cortisone to cortisol in adipose tissue of obese individuals (Engeli, et al., (2004) *Obes. Res.* 12: 9-17).

A new class of 11βHSD1 inhibitors, the arylsulfonamidothiazoles, was shown to improve hepatic insulin sensitivity and reduce blood glucose levels in hyperglycemic strains of mice (Barf et al. (2002) *J. Med. Chem.* 45: 3813-3815; Alberts et al. *Endocrinology* (2003) 144: 4755-4762). Additionally, it was recently reported that these selective inhibitors of 11βHSD1 can ameliorate severe hyperglycemia in genetically diabetic obese mice. Data using a structurally distinct series of compounds, the adamantyl triazoles (Hermanowski-Vosatka et al. (2005) *J. Exp. Med.* 202: 517-527), also indicates efficacy in rodent models of insulin resistance and diabetes, and further illustrates efficacy in a mouse model of atherosclerosis, perhaps suggesting local effects of corticosterone in the rodent vessel wall. Thus, 11βHSD1 is a promising pharmaceutical target for the treatment of the Metabolic Syndrome (Masuzaki, et al., (2003) *Curr. Drug Targets Immune Endocr. Metabol. Disord.* 3: 255-62).

A. Obesity and Metabolic Syndrome

As described above, multiple lines of evidence suggest that inhibition of 11βHSD1 activity can be effective in combating obesity and/or aspects of the metabolic syndrome cluster, including glucose intolerance, insulin resistance, hyperglycemia, hypertension, hyperlipidemia, and/or atherosclerosis/coronary heart disease. Glucocorticoids are known antagonists of insulin action, and reductions in local glucocorticoid levels by inhibition of intracellular cortisone to cortisol conversion should increase hepatic and/or peripheral insulin sensitivity and potentially reduce visceral adiposity. As described above, 11βHSD1 knockout mice are resistant to hyperglycemia, exhibit attenuated induction of key hepatic gluconeogenic enzymes, show markedly increased insulin sensitivity within adipose, and have an improved lipid profile. Additionally, these animals show resistance to high fat diet-induced obesity (Kotelevstev et al. (1997) *Proc. Natl. Acad. Sci.* 94: 14924-14929; Morton et al. (2001) *J. Biol. Chem.* 276: 41293-41300; Morton et al. (2004) *Diabetes* 53: 931-938). In vivo pharmacology studies with multiple chemical scaffolds have confirmed the critical role for 11bHSD1 in regulating insulin resistance, glucose intolerance, dyslipidemia, hypertension, and atherosclerosis. Thus, inhibition of 11βHSD1 is predicted to have multiple beneficial effects in the liver, adipose, skeletal muscle, and heart, particularly related to alleviation of component(s) of the metabolic syndrome, obesity, and/or coronary heart disease.

B. Pancreatic Function

Glucocorticoids are known to inhibit the glucose-stimulated secretion of insulin from pancreatic beta-cells (Billaudel and Sutter (1979) *Horm. Metab. Res.* 11: 555-560). In both Cushing's syndrome and diabetic Zucker fa/fa rats, glucose-stimulated insulin secretion is markedly reduced (Ogawa et al. (1992) *J. Clin. Invest.* 90: 497-504). 11βHSD1 mRNA and activity has been reported in the pancreatic islet cells of ob/ob mice and inhibition of this activity with carbenoxolone, an 11βHSD1 inhibitor, improves glucose-stimulated insulin release (Davani et al. (2000) *J. Biol. Chem.* 275: 34841-34844). Thus, inhibition of 11βHSD1 is predicted to have beneficial effects on the pancreas, including the enhancement of glucose-stimulated insulin release and the potential for attenuating pancreatic beta-cell decompensation.

C. Cognition and Dementia

Mild cognitive impairment is a common feature of aging that may be ultimately related to the progression of dementia. In both aged animals and humans, inter-individual differences in general cognitive function have been linked to variability in the long-term exposure to glucocorticoids (Lupien et al. (1998) *Nat. Neurosci.* 1: 69-73). Further, dysregulation of the HPA axis resulting in chronic exposure to glucocorticoid excess in certain brain subregions has been proposed to contribute to the decline of cognitive function (McEwen and Sapolsky (1995) *Curr. Opin. Neurobiol.* 5: 205-216). 11βHSD1 is abundant in the brain, and is expressed in multiple subregions including the hippocampus, frontal cortex, and cerebellum (Sandeep et al. (2004) *Proc. Natl. Acad. Sci. Early Edition:* 1-6). Treatment of primary hippocampal cells with the 11βHSD1 inhibitor carbenoxolone protects the cells from glucocorticoid-mediated exacerbation of excitatory amino acid neurotoxicity (Rajan et al. (1996) *J. Neurosci.* 16: 65-70). Additionally, 11βHSD1-deficient mice are protected from glucocorticoid-associated hippocampal dysfunction that is associated with aging (Yau et al. (2001) *Proc. Natl. Acad. Sci.* 98: 4716-4721). In two randomized, double-blind, placebo-controlled crossover studies, administration of carbenoxolone improved verbal fluency and verbal memory (Sandeep et al. (2004) *Proc. Natl. Acad. Sci. Early Edition:* 1-6). Thus, inhibition of 11βHSD1 is predicted to reduce exposure to glucocorticoids in the brain and protect against deleterious glucocorticoid effects on neuronal function, including cognitive impairment, dementia, and/or depression.

D. Intra-Ocular Pressure

Glucocorticoids can be used topically and systemically for a wide range of conditions in clinical ophthalmology. One particular complication with these treatment regimens is corticosteroid-induced glaucoma. This pathology is characterized by a significant increase in intra-ocular pressure (IOP). In its most advanced and untreated form, IOP can lead to partial visual field loss and eventually blindness. IOP is produced by the relationship between aqueous humor production and drainage. Aqueous humor production occurs in the non-pigmented epithelial cells (NPE) and its drainage is through the cells of the trabecular meshwork. 11βHSD1 has been localized to NPE cells (Stokes et al. (2000) *Invest. Ophthalmol. Vis. Sci.* 41: 1629-1683; Rauz et al. (2001) *Invest. Ophthalmol. Vis. Sci.* 42: 2037-2042) and its function is likely relevant to the amplification of glucocorticoid activity within these cells. This notion has been confirmed by the observation that free cortisol concentration greatly exceeds that of cortisone in the aqueous humor (14:1 ratio). The functional significance of 11βHSD1 in the eye has been evaluated using the inhibitor carbenoxolone in healthy volunteers (Rauz et al. (2001) *Invest. Ophthalmol. Vis. Sci.* 42: 2037-2042). After seven days of carbenoxolone treatment, IOP was reduced by 18%. Thus, inhibition of 11βHSD1 in the eye is predicted to reduce local glucocorticoid concentrations and IOP, producing beneficial effects in the management of glaucoma and other visual disorders.

E. Hypertension

Adipocyte-derived hypertensive substances such as leptin and angiotensinogen have been proposed to be involved in the pathogenesis of obesity-related hypertension (Matsuzawa et al. (1999) *Ann. N.Y. Acad. Sci.* 892: 146-154; Wajchenberg (2000) *Endocr. Rev.* 21: 697-738). Leptin, which is secreted in excess in aP2-11βHSD1 transgenic mice (Masuzaki et al. (2003) *J. Clinical Invest.* 112: 83-90), can activate various sympathetic nervous system pathways, including those that regulate blood pressure (Matsuzawa et al. (1999) *Ann. N.Y. Acad. Sci.* 892: 146-154). Additionally, the renin-angiotensin system (RAS) has been shown to be a major determinant of blood pressure (Walker et al. (1979) *Hypertension* 1: 287-291). Angiotensinogen, which is produced in liver and adipose tissue, is the key substrate for renin and drives RAS activation. Plasma angiotensinogen levels are markedly elevated in aP2-11βHSD1 transgenic mice, as are angiotensin II and aldosterone (Masuzaki et al. (2003) *J. Clinical Invest.* 112: 83-90). These forces likely drive the elevated blood pressure observed in aP2-11βHSD1 transgenic mice. Treatment of these mice with low doses of an angiotensin II receptor antagonist abolishes this hypertension (Masuzaki et al. (2003) *J. Clinical Invest.* 112: 83-90). This data illustrates the importance of local glucocorticoid reactivation in adipose tissue and liver, and suggests that hypertension may be caused or exacerbated by 11βHSD1 activity. Thus, inhibition of 11βHSD1 and reduction in adipose and/or hepatic glucocorticoid levels is predicted to have beneficial effects on hypertension and hypertension-related cardiovascular disorders.

F. Bone Disease

Glucocorticoids can have adverse effects on skeletal tissues. Continued exposure to even moderate glucocorticoid doses can result in osteoporosis (Cannalis (1996) *J. Clin. Endocrinol. Metab.* 81: 3441-3447) and increased risk for fractures. Experiments in vitro confirm the deleterious effects of glucocorticoids on both bone-resorbing cells (also known as osteoclasts) and bone forming cells (osteoblasts). 11βHSD1 has been shown to be present in cultures of human primary osteoblasts as well as cells from adult bone, likely a mixture of osteoclasts and osteoblasts (Cooper et al. (2000) *Bone* 27: 375-381), and the 11βHSD1 inhibitor carbenoxolone has been shown to attenuate the negative effects of glucocorticoids on bone nodule formation (Bellows et al. (1998) *Bone* 23: 119-125). Thus, inhibition of 11βHSD1 is predicted to decrease the local glucocorticoid concentration within osteoblasts and osteoclasts, producing beneficial effects in various forms of bone disease, including osteoporosis.

Small molecule inhibitors of 11βHSD1 are currently being developed to treat or prevent 11βHSD1-related diseases such as those described above. For example, certain amide-based inhibitors are reported in WO 2004/089470, WO 2004/089896, WO 2004/056745, and WO 2004/065351. Certain antagonists of 11βHSD1 have also been evaluated in human clinical trials (Kurukulasuriya, et al., (2003) *Curr. Med. Chem.* 10: 123-53). In light of the experimental data indicating a role for 11βHSD1 in glucocorticoid-related disorders, metabolic syndrome, hypertension, obesity, insulin resistance, hyperglycemia, hyperlipidemia, type 2 diabetes, atherosclerosis, androgen excess (hirsutism, menstrual irregularity, hyperandrogenism) and polycystic ovary syndrome (PCOS), therapeutic agents aimed at augmentation or suppression of these metabolic pathways by modulating glucocorticoid signal transduction at the level of 11βHSD1 are desirable.

Furthermore, because the MR binds to aldosterone (its natural ligand) and cortisol with equal affinities, compounds that are designed to interact with the active site of 11βHSD1 (which binds to cortisone/cortisol) may also interact with the MR and act as antagonists. Because the MR is implicated in heart failure, hypertension, and related pathologies including atherosclerosis, arteriosclerosis, coronary artery disease, thrombosis, angina, peripheral vascular disease, vascular wall damage, and stroke, MR antagonists are desirable and may also be useful in treating complex cardiovascular, renal, and inflammatory pathologies including disorders of lipid metabolism including dyslipidemia or hyperlipoproteinaemia, diabetic dyslipidemia, mixed dyslipidemia, hypercholesterolemia, hypertriglyceridemia, as well as those associated with type 1 diabetes, type 2 diabetes, obesity, metabolic syndrome, and insulin resistance, and general aldosterone-related target-organ damage.

As evidenced herein, there is a continuing need for new and improved drugs that target 11βHSD1. The compounds, compositions and methods therein help meet this and other needs.

SUMMARY

The present invention provides, inter alia, compounds of Formula I:

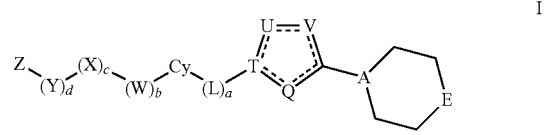

or a pharmaceutically acceptable salt or a prodrug thereof, wherein constituent members are defined herein.

The present invention further provides compounds of Formula I as isolated compounds.

The present invention further provides a composition comprising at least one compound of the invention, or pharmaceutically acceptable salt thereof, and at least one pharmaceutically acceptable carrier.

The present invention further provides methods of modulating 11βHSD1 by contacting 11βHSD1 with a compound of the invention, or pharmaceutically acceptable salt thereof.

The present invention further provides methods of inhibiting 11βHSD1 by contacting 11βHSD1 with a compound of the invention, or pharmaceutically acceptable salt thereof.

The present invention further provides methods of inhibiting the conversion of cortisone to cortisol in a cell by contacting the cell with a compound of the invention, or pharmaceutically acceptable salt thereof.

The present invention further provides methods of inhibiting the production of cortisol in a cell by contacting the cell with a compound of the invention, or pharmaceutically acceptable salt thereof.

The present invention further provides methods of treating diseases associated with activity or expression of 11βHSD1

The details of one or more embodiments of the invention are set forth in the description below. Other features, objects, and advantages of the invention will be apparent from the description and from the claims.

DETAILED DESCRIPTION

The present invention provides, inter alia, compounds of Formula I:

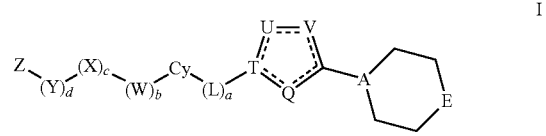

or a pharmaceutically acceptable salt or a prodrug thereof, wherein:

A is CH or N;

E is O or $C(OR^{E1})R^{E2}$;

R$^{E1}$ and R$^{E2}$ are independently selected from H, (C$_{1-6}$)alkyl, (C$_{2-6}$)alkenyl, (C$_{2-6}$)alkynyl, aryl, and heteroaryl, wherein R$^{E1}$ that is aryl or heteroaryl is optionally substituted with OH, NH$_2$, halogen, (C$_{1-7}$)hydrocarbyl, (C$_{1-6}$)haloalkyl, heteroaryl, heteroaryl(C$_{1-3}$)alkyl, heterocycloalkyl, or heterocycloalkyl(C$_{1-3}$)alkyl;

Q is O, S, N, NR$^1$, CR$^1$ or CR$^{1a}$R$^{1b}$;

T is C or N;

U is O, S, N, NR$^{1c}$ or CR$^{1d}$;

V is O, S, N, NR$^{1e}$ or CR$^{1f}$;

----- is a single or double bond;

R$^1$, R$^{1a}$, R$^{1b}$, R$^{1c}$, R$^{1d}$, R$^{1e}$ and R$^{1f}$ are independently selected from H, (C$_{1-6}$)alkyl and (C$_{1-6}$)cycloalkyl; wherein R$^1$, R$^{1a}$, R$^{1b}$, R$^{1c}$, R$^{1d}$, R$^{1e}$ or R$^{1f}$ that is (C$_{1-6}$)alkyl or (C$_{3-6}$)cycloalkyl is optionally substituted by 1, 2 or 3 substituents independently selected from halogen, CF$_3$, OH, (C$_{1-6}$)alkoxy, (C$_{3-6}$)cycloalkyl, and heterocycloalkyl;

L is (CR$^2$R$^3$)$_m$ or (CR$^2$R$^3$)$_n$-J-(CR$^2$R$^3$)$_p$;

R$^2$ and R$^3$ are independently selected from H and (C$_{1-6}$)alkyl; wherein R$^2$ and R$^3$ that are (C$_{1-6}$)alkyl are optionally substituted by 1, 2 or 3 substituents independently selected from halogen, CN, and OR$^4$;

or R$^2$ and R$^3$, together with the carbon atom to which they are attached, form a 3-, 4-, 5-, 6- or 7-membered cycloalkyl ring or a 3-, 4-, 5-, 6- or 7-membered heterocycloalkyl ring, each optionally substituted by 1, 2 or 3 substituents independently selected from halogen, CN, and OR$^4$;

n, m and p are independently selected from 0, 1, 2, 3 and 4;

J is selected from O, S, SO$_v$, C(=O), NR$^4$, NR$^4$C(=O), NR$^4$SO$_2$, NR$^4$C(=O)NR$^4$, C(=O)O, and OC(=O);

v is 1 or 2;

R$^4$ is independently selected from H, (C$_{1-6}$)alkyl, (C$_{1-6}$)cycloalkyl, and (C$_{1-6}$)cycloalkyl(C$_{1-4}$)alkyl;

Cy is arylene, heteroarylene, heterocycloalkylene, or cycloalkylene, each optionally substituted by 1, 2 or 3 substituents independently selected from halogen, (C$_{1-4}$)alkyl, (C$_{2-4}$)alkenyl, (C$_{2-4}$)alkynyl, (C$_{1-4}$)haloalkyl, CN, NO$_2$, OR$^a$, SR$^a$, C(=O)OR$^a$, (O)$_u$C(=O)R$^b$, (O)$_u$C(=O)NR$^c$R$^d$, NR$^c$R$^d$, NR$^c$C(=O)R$^b$, NR$^c$C(=O)OR$^a$, SO$_v$R$^b$, and SO$_v$NR$^c$R$^d$;

u is 0 or 1;

R$^a$ is independently selected from H, (C$_{1-10}$)hydrocarbyl, C(=O)(C$_{1-10}$)hydrocarbyl, (C$_{1-6}$)haloalkyl, heteroaryl, heteroaryl(C$_{1-3}$)alkyl, heterocycloalkyl, and heterocycloalkyl(C$_{1-3}$)alkyl; wherein R$^a$ that is (C$_{1-10}$)hydrocarbyl, (C$_{1-6}$)haloalkyl, heteroaryl, heteroaryl(C$_{1-3}$)alkyl, heterocycloalkyl, or heterocycloalkyl(C$_{1-3}$)alkyl is optionally substituted with OH, NH$_2$, halogen, CN, (C$_{1-7}$)hydrocarbyl, (C$_{1-6}$)haloalkyl, (C$_{1-6}$)alkoxy, heteroaryl, heteroaryl(C$_{1-3}$)alkyl, heterocycloalkyl, or heterocycloalkyl(C$_{1-3}$)alkyl;

R$^b$ is independently selected from H, (C$_{1-10}$)hydrocarbyl, (C$_{1-6}$)haloalkyl, heteroaryl, heteroaryl(C$_{1-3}$)alkyl, heterocycloalkyl, and heterocycloalkyl(C$_{1-3}$)alkyl; wherein R$^b$ that is (C$_{1-10}$)hydrocarbyl, (C$_{1-6}$)haloalkyl, heteroaryl, heteroaryl (C$_{1-3}$)alkyl, heterocycloalkyl, or heterocycloalkyl(C$_{1-3}$)alkyl is optionally substituted with OH, NH$_2$, halogen, CN, (C$_{1-7}$)hydrocarbyl, (C$_{1-6}$)haloalkyl, (C$_{1-6}$)alkoxy, heteroaryl, heteroaryl(C$_{1-3}$)alkyl, heterocycloalkyl, or heterocycloalkyl (C$_{1-3}$)alkyl;

R$^c$ and R$^d$ are independently selected from H, (C$_{1-10}$)hydrocarbyl, (C$_{1-6}$)haloalkyl, heteroaryl, heteroaryl(C$_{1-3}$)alkyl, heterocycloalkyl, and heterocycloalkyl(C$_{1-3}$)alkyl; wherein R$^c$ and R$^d$ that are (C$_{1-10}$)hydrocarbyl, (C$_{1-6}$)haloalkyl, heteroaryl, heteroaryl(C$_{1-3}$)alkyl, heterocycloalkyl or heterocycloalkyl(C$_{1-3}$)alkyl are optionally substituted with OH, NH$_2$, halogen, CN, (C$_{1-7}$)hydrocarbyl, (C$_{1-6}$)haloalkyl, (C$_{1-6}$)alkoxy, heteroaryl, heteroaryl(C$_{1-3}$)alkyl, heterocycloalkyl, or heterocycloalkyl(C$_{1-3}$)alkyl;

or R$^c$ and R$^d$, together with the N atom to which they are attached, form a 4-, 5-, 6- or 7-membered heterocycloalkyl ring;

W is selected from (C$_{1-6}$)hydrocarbylene, O, SO$_v$, NR$^e$, C(=O), C(=O)O, C(=O)NR$^e$, SO$_v$NR$^e$ and NR$^e$C(=O)NR$^e$; wherein W that is (C$_{1-6}$)hydrocarbylene is optionally substituted by 1, 2 or 3 substituents independently selected from halogen, OR$^f$ and NR$^f{}_2$;

R$^e$ is independently selected from H, (C$_{1-10}$)hydrocarbyl, C(=O)(C$_{1-10}$)hydrocarbyl, (C$_{1-6}$)haloalkyl, heteroaryl, heteroaryl(C$_{1-3}$)alkyl, heterocycloalkyl and heterocycloalkyl (C$_{1-3}$)alkyl; wherein R$^e$ that is (C$_{1-10}$)hydrocarbyl, (C$_{1-6}$)haloalkyl, heteroaryl, heteroaryl(C$_{1-3}$)alkyl, heterocycloalkyl or heterocycloalkyl(C$_{1-3}$)alkyl is optionally substituted with OH, NH$_2$, halogen, (C$_{1-7}$)hydrocarbyl, (C$_{1-6}$)haloalkyl, heteroaryl, heteroaryl(C$_{1-3}$)alkyl, heterocycloalkyl or heterocycloalkyl(C$_{1-3}$)alkyl;

R$^f$ is independently selected from H, (C$_{1-4}$)alkyl, and (C$_{1-4}$)haloalkyl;

X is selected from (C$_{1-6}$)hydrocarbylene, arylene, heteroarylene, and heterocycloalkylene; wherein X that is (C$_{1-6}$)hydrocarbylene, arylene, heteroarylene, or heterocycloalkylene is optionally substituted by 1, 2 or 3 substituents independently selected from halogen, (C$_{1-6}$)alkyl, (C$_{2-6}$)alkenyl, (C$_{2-6}$)alkynyl, (C$_{1-4}$)haloalkyl, CN, NO$_2$, OR$^f$, and NR$^f{}_2$;

Y is selected from (C$_{1-6}$)hydrocarbylene, O, SO$_v$, NR$^e$, C(=O), C(=O)O, C(=O)NR$^e$, SO$_v$NR$^e$, or NR$^e$C(=O)NR$^e$; wherein Y that is (C$_{1-6}$)hydrocarbylene is optionally substituted by 1, 2 or 3 substituents independently selected from halogen, OR$^f$, and NR$^f{}_2$;

Z is selected from H, halogen, CN, NO$_2$, OR$^f$, NR$^f{}_2$, (C$_{1-14}$)hydrocarbyl, heteroaryl and heterocycloalkyl; wherein Z that is (C$_{1-14}$)hydrocarbyl, heterocycloalkyl or heteroaryl is optionally substituted by 1, 2 or 3 substituents independently selected from halogen, (C$_{1-6}$)hydrocarbyl, (C$_{1-4}$)haloalkyl, aryl, heteroaryl, heterocycloalkyl, CN, NO$_2$, OR$^a$, SR$^a$, (O)$_u$C(=O)R$^b$, (O)$_u$C(=O)NR$^c$R$^d$, (O)$_u$C(=O)(O)$_u$R$^a$, NR$^c$R$^d$, NR$^c$C(=O)R$^b$, NR$^c$C(=O)OR$^a$, NR$^c$SO$_2$R$^b$, SO$_v$R$^b$, and SO$_v$NR$^c$R$^d$; and a, b, c and d are independently selected from 0 and 1.

In some embodiments, the compound of Formula I is other than 1-(4-methyl-5-(1-phenylcyclopropyl)-4H-1,2,4-triazol-3-yl)piperidin-4-ol; 4-(4-methyl-5-(1-phenylcyclopropyl)-4H-1,2,4-triazol-3-yl)morpholine; or 3-(1-adamantyl)-4-methyl-5-(tetrahydro-2H-pyran-4-yl)-4H-1,2,4-triazole.

In some embodiments, U and V are both N; T is C; and Q is N—R$^1$.

In some embodiments, U is N; V is O; T is C; and Q is C—R$^1$.

In some embodiments, U is O; V is N; T is C; and Q is C—R$^1$.

In some embodiments, U is N; V is O; T is C; and Q is CR$^{1a}$R$^{1b}$.

In some embodiments, T, U and V are N; and Q is C—R$^1$.

In some embodiments, U is O; V and Q are N; and T is C.

In some embodiments, V is O; U and Q are N; and T is C.

In some embodiments, U and V are both N; T is C; and Q is C—R$^1$.

In some embodiments, U is N; T and V are C; and Q is NR$^1$.

In some embodiments, U is N; V and T are C; and Q is O.

In some embodiments, U is O; V and T are C; and Q is N.

In some embodiments, U is N, V and T are C; and Q is S.

In some embodiments, U and V are both N; T is C; and Q is O.

In some embodiments, U and V are both N; T is C; and Q is S.

In some embodiments, at least one of U and V is N.

In some embodiments, the ring containing U, V, T and Q is a five-membered aromatic ring. In some embodiments, the ring containing U, V, T and Q is a five-membered ring containing one double bond. In some embodiments, the ring containing U, V, T and Q is selected from a 1,2,4-triazole ring, an isoxazole ring, a 1,2,3-triazole ring, a 1,2,4-triazole ring, 1,2,4-oxadiazole ring, a pyrazole ring, a 1H-imidazole ring, an oxazole ring, a thiazole ring, a 1,3,4-oxadiazole ring, and a 1,3,4-thiadiazole ring.

In some embodiments, A is CH. In some embodiments, A is N.

In some embodiments, E is O. In some embodiments, E is $C(OH)R^{E1}$. In some embodiments, E is $C(OR^{E1})R^{E2}$. In some embodiments, $R^{E1}$ is H. In some embodiments, $R^{E1}$ and $R^{E2}$ are both H. In some embodiments, E is C(OH)H.

In some embodiments, Q is O, S, N, $NR^1$ or $CR^1$. In some embodiments, Q is O, N, $NR^1$ or $CR^1$. In some embodiments, Q is O, $NR^1$ or $CR^1$. In some embodiments, Q is $NR^1$ or $CR^1$. In some embodiments, Q is $NR^1$.

In some embodiments, T is C. In some embodiments, T is N.

In some embodiments, U is O. In some embodiments, U is S. In some embodiments, U is N. In some embodiments, U is $NR^{1c}$. In some embodiments, U is $CR^{1d}$.

In some embodiments, V is O. In some embodiments, V is S. In some embodiments, V is N. In some embodiments, V is $NR^{1c}$. In some embodiments, V is $CR^{1d}$.

In some embodiments, $R^1$, $R^{1a}$, $R^{1b}$, $R^{1c}$, $R^{1d}$, $R^{1e}$, and $R^{1f}$ are independently selected from H and $(C_{1-6})$alkyl; wherein $R^1$, $R^{1a}$, $R^{1b}$, $R^{1c}$, $R^{1d}$, $R^{1e}$ or $R^{1f}$ that is $(C_{1-6})$alkyl is optionally substituted by 1, 2 or 3 substituents independently selected from halogen, $CF_3$, OH, $(C_{1-6})$alkoxy, $(C_{1-6})$cycloalkyl and heterocycloalkyl;

In some embodiments, L is $(CR^2R^3)_m$.

In some embodiments, L is $(CR^2R^3)$.

In some embodiments, L is $(CR^2R^3)$ and $R^2$ and $R^3$, together with the carbon atom to which they are attached, form a 3-, 4-, 5-, 6- or 7-membered cycloalkyl ring or a 3-, 4-, 5-, 6- or 7-membered heterocycloalkyl ring, each optionally substituted by 1, 2 or 3 substituents independently selected from halogen, CN and $OR^4$.

In some embodiments, L is $(CR^2R^3)$ and $R^2$ and $R^3$, together with the carbon atom to which they are attached, form cyclopropyl optionally substituted by 1, 2 or 3 substituents independently selected from halogen, CN and $OR^4$.

In some embodiments, L is $(CR^2R^3)$ and $R^2$ and $R^3$, together with the carbon atom to which they are attached, form cyclopropyl.

In some embodiments, L is $(CR^2R^3)_n$-J-$(CR^2R^3)_p$.

In some embodiments, m is 0. In some embodiments, m is 1. In some embodiments, m is 2. In some embodiments, m is 3.

In some embodiments, n is 0. In some embodiments, n is 1. In some embodiments, n is 2. In some embodiments, n is 3.

In some embodiments, p is 0. In some embodiments, p is 1. In some embodiments, p is 2. In some embodiments, p is 3.

In some embodiments $R^2$ and $R^3$, together with the carbon atom to which they are attached, form a 3-membered cycloalkyl ring. In some embodiments $R^2$ and $R^3$, together with the carbon atom to which they are attached, form a 4-membered cycloalkyl ring. In some embodiments $R^2$ and $R^3$, together with the carbon atom to which they are attached, form a 5-membered cycloalkyl ring. In some embodiments $R^2$ and $R^3$, together with the carbon atom to which they are attached, form a 6-membered cycloalkyl ring. In some embodiments $R^2$ and $R^3$, together with the carbon atom to which they are attached, form a 7-membered cycloalkyl ring. In some embodiments, the cycloalkyl ring is optionally substituted by 1, 2, or 3 substituents independently selected from halogen and $OR^4$. In some embodiments, the cycloalkyl ring is optionally substituted by 1, 2, or 3 substituents independently selected from halogen.

In some embodiments $R^2$ and $R^3$, together with the carbon atom to which they are attached, form a 4-, 5- or 6-membered cycloalkyl ring substituted substituted by 1, 2 or 3 substituents independently selected from halogen, CN, and $OR^4$. In some embodiments $R^2$ and $R^3$, together with the carbon atom to which they are attached, form a 4-, 5- or 6-membered cycloalkyl ring substituted substituted by 1, 2 or 3 substituents independently selected from halogen and $OR^4$. In some embodiments $R^2$ and $R^3$, together with the carbon atom to which they are attached, form a 4-, 5- or 6-membered cycloalkyl ring substituted substituted by 1, 2, or 3 halogen atoms. In some embodiments $R^2$ and $R^3$, together with the carbon atom to which they are attached, form a 4-, 5- or 6-membered cycloalkyl ring substituted substituted by 1, 2 or 3 fluorine atoms. In some embodiments $R^2$ and $R^3$, together with the carbon atom to which they are attached, form a 4-membered cycloalkyl ring substituted substituted by a fluorine atom.

In some embodiments $R^2$ and $R^3$, together with the carbon atom to which they are attached form a 3-membered heterocycloalkyl ring. In some embodiments $R^2$ and $R^3$, together with the carbon atom to which they are attached form a 4-membered heterocycloalkyl ring. In some embodiments $R^2$ and $R^3$, together with the carbon atom to which they are attached form a 5-membered heterocycloalkyl ring. In some embodiments $R^2$ and $R^3$, together with the carbon atom to which they are attached form a 6-membered heterocycloalkyl ring. In some embodiments $R^2$ and $R^3$, together with the carbon atom to which they are attached form a 7-membered heterocycloalkyl ring.

In some embodiments, $R^2$ and $R^3$, together with the carbon to which they are attached, form a cyclopropane ring; Cy is phenyl optionally substituted with halogen; b, c and d are 0; and Z is selected from H, halogen, CN, $OR^f$ and $(C_{1-6})$hydrocarbyl.

In some embodiments, $R^2$ and $R^3$, together with the carbon to which they are attached, form a cyclopropane ring; Cy is phenyl optionally substituted with halogen; b, c and d are 0; and Z is halogen.

In some embodiments, $R^2$ and $R^3$, together with the carbon to which they are attached, form a cyclopropane ring; Cy is phenyl optionally substituted with halogen; b, c and d are 0; and Z is heteroaryl or heterocyloalkyl optionally substituted by $C(=O)NR^cR^d$.

In some embodiments, $R^2$ and $R^3$, together with the carbon to which they are attached, form a cyclopropane ring; Cy is phenyl optionally substituted with halogen; b, c and d are 0; and Z is pyridinyl optionally substituted by $C(=O)NR^cR^d$.

In some embodiments, $R^2$ and $R^3$, together with the carbon to which they are attached, form a cyclopropane ring; Cy is phenyl optionally substituted with halogen; b, c and d are 0; and Z is pyrazolyl optionally substituted by $C(=O)NR^cR^d$.

In some embodiments, $R^2$ and $R^3$, together with the carbon to which they are attached, form a cyclopropane ring; Cy is phenyl optionally substituted with halogen; b, c and d are 0; and Z is piperazinyl optionally substituted by $C(=O)OR^a$.

In some embodiments, $R^2$ and $R^3$, together with the carbon to which they are attached, form a cyclopropane ring; Cy is phenyl optionally substituted with halogen; W is O; c and d are 0; and Z is heteroaryl optionally substituted by halogen, CN, $OR^a$, $SR^a$, $(C_{1-6})$hydrocarbyl or $(C_{1-4})$haloalkyl.

In some embodiments, a is 0; Cy is bicyclo[2,2,2]octanenyl; b is 0; X is heteroaryl, d is 0; and Z is aryl optionally substituted by halogen, CN, $OR^a$, $SR^a$, $(C_{1-6})$hydrocarbyl, $(C_{1-4})$haloalkyl.

In some embodiments, a is 0; Cy is bicycle[2,2,2]octanenyl; b is 0; X is 1,2,4-oxadizolyl, d is 0; and Z is phenyl optionally substituted by halogen, CN, $OR^a$, $SR^a$, $(C_{1-6})$hydrocarbyl, $(C_{1-4})$haloalkyl.

In some embodiments, J is O. In some embodiments, J is S. In some embodiments, J is $SO_v$. In some embodiments, J is $C(=O)$. In some embodiments, J is $NR^4$. In some embodiments, J is $NR^4C(=O)$. In some embodiments, J is $NR^4SO_2$. In some embodiments, J is $NR^4C(=O)NR^4$. In some embodiments, J is $C(=O)O$. In some embodiments, J is $OC(=O)$ In some embodiments, v is 1. In some embodiments, v is 2.

In some embodiments, $R^4$ is H. In some embodiments, $R^4$ is $(C_{1-6})$alkyl. In some embodiments, $R^4$ is $(C_{3-6})$cycloalkyl. In some embodiments, $R^4$ is $(C_{3-6})$cycloalkyl$(C_{1-4})$alkyl.

In some embodiments, Cy is arylene or heteroarylene, each optionally substituted by 1, 2 or 3 substituents independently selected from halogen, $(C_{1-4})$alkyl, $(C_{2-4})$alkenyl, $(C_{2-4})$alkynyl, $(C_{1-4})$haloalkyl, CN, $NO_2$, $OR^a$, $SR^a$, $C(=O)OR^a$, $(O)_uC(=O)R^b$, $(O)_uC(=O)NR^cR^d$, $NR^cR^d$, $NR^cC(=O)R^b$, $NR^cC(=O)OR^a$, $SO_vR^b$ and $SO_vNR^cR^d$.

In some embodiments, Cy is arylene optionally substituted by 1, 2 or 3 substituents independently selected from halogen, $(C_{1-4})$alkyl, $(C_{2-4})$alkenyl, $(C_{2-4})$alkynyl, $(C_{1-4})$haloalkyl, CN, $NO_2$, $OR^a$, $SR^a$, $C(=O)OR^a$, $(O)_uC(=O)R^b$, $(O)_uC(=O)NR^cR^d$, $NR^cR^d$, $NR^cC(=O)R^b$, $NR^cC(=O)OR^a$, $SO_vR^b$ and $SO_vNR^cR^d$.

In some embodiments, Cy is phenyl optionally substituted by 1, 2 or 3 substituents independently selected from halogen, $(C_{1-4})$alkyl, $(C_{2-4})$alkenyl, $(C_{2-4})$alkynyl, $(C_{1-4})$haloalkyl, CN, $NO_2$, $OR^a$, $SR^a$, $C(=O)OR^a$, $(O)_uC(=O)R^b$, $(O)_uC(=O)NR^cR^d$, $NR^cR^d$, $NR^cC(=O)R^b$, $NR^cC(=O)OR^a$, $SO_vR^b$ and $SO_vNR^cR^d$.

In some embodiments, Cy is arylene. In some embodiments, Cy is phenyl.

In some embodiments, Cy is heteroarylene. In some embodiments, Cy is a 5-membered heteroarylene. In some embodiments, Cy is 5-membered heteroarylene selected from pyrrole, furan, thiophene, imidazole, pyrazole, oxazole, isoxazole, thiazole, 1,2,3-triazole, 1,2,4-triazole, oxadiazole, and thiadiazole.

In some embodiments, Cy is a 6-membered heteroarylene. In some embodiments, Cy is 5-membered heteroarylene selected from pyridine, pyrazine, triazine, piperazine and pyrimidine.

In some embodiments, Cy is a bicyclic heteroarylene. In some embodiments, Cy is a bicyclic heteroarylene selected from indole, benzimidazole, benzotriazole, benzoxazole, benzthiazole, quinoline, isoquinoline, quinazoline, cinnoline, quinolizidine, and pyrrolizidine.

In some embodiments, Cy is heterocycloalkylene. In some embodiments, Cy is heterocycloalkylene selected from morpholine, thiomorpholine, piperazine, tetrahydrofuran, tetrahydrothiophene, 2,3-dihydrobenzofuran, 1,3-benzodioxole, benzo-1,4-dioxane, piperidine, pyrrolidine, isoxazolidine, isothiazolidine, pyrazolidine, oxazolidine, thiazolidine and imidazolidine.

In some embodiments, Cy is cycloalkylene optionally substituted by 1, 2 or 3 substituents selected from halogen, $(C_{1-4})$alkyl, $(C_{1-4})$haloalkyl, CN and $OR^a$. In some embodiments, Cy is bicyclo[2,2,2]octanenyl, optionally substituted by 1, 2 or 3 substituents selected from halogen, $(C_{1-4})$alkyl, $(C_{1-4})$haloalkyl, CN and $OR^a$.

In some embodiments, Cy is arylene optionally substituted by 1, 2 or 3 substituents selected from halogen, $(C_{1-4})$alkyl, $(C_{1-4})$haloalkyl, CN, $OR^a$.

In some embodiments, a is 0. In some embodiments, b is 0. In some embodiments, c is 0. In some embodiments, d is 0.

In some embodiments, a, b, c and d are all 0. In some embodiments, the sum of a, b, c and d is greater than 0. In some embodiments, the sum of a, b, c and d is 1. In some embodiments, the sum of a, b, c and d is greater than 1. In some embodiments, the sum of a, b, c and d is 2. In some embodiments, the sum of a, b, c and d is greater than 2. In some embodiments, the sum of a, b, c and d is 3. In some embodiments, the sum of a, b, c and d is greater than 3.

In some embodiments, b, c, and d are all 0; and Z is selected from H, halogen, CN, $OR^f$, $(C_{1-14})$hydrocarbyl, heteroaryl and heterocycloalkyl. In some sub-embodiments thereof, Z is H, halogen, CN or $(C_{1-14})$hydrocarbyl. In some embodiments, Z that is $(C_{1-14})$hydrocarbyl, heteroaryl or heterocycloalkyl is optionally substituted by 1, 2 or 3 substituents independently selected from halogen, $(C_{1-6})$hydrocarbyl, $(C_{1-4})$haloalkyl, aryl, heteroaryl, heterocycloalkyl, CN, $OR^a$, $C(O)_u(NR^cR^d)$ and $(O)_uC(=O)(O)_u$.

In some embodiments, Z is heteroaryl or heterocycloalkyl, each optionally substituted by 1 or 2 substituents selected from halogen, $(C_{1-4})$haloalkyl, CN, $OR^a$, $C(O)_u(NR^cR^d)$ and $(O)_uC(=O)(O)_u$.

In some embodiments, W is O; c and d are 0; and Z is selected from $(C_{1-14})$hydrocarbyl, heteroaryl and heterocycloalkyl; wherein each $(C_{1-14})$hydrocarbyl, heteroaryl or heterocycloalkyl is optionally substituted by 1, 2, or 3 substituents independently selected from halogen, CN, $OR^a$, $C(O)_u(NR^cR^d)$ and $(O)_uC(=O)(O)_u$. In some sub-embodiments thereof, a is 0.

In some embodiments, W is selected from $(C_{1-6})$hydrocarbylene, O, $SO_v$, $C(=O)$, $C(=O)NR^e$, $SO_vNR^e$, or $NR^eC(=O)NR^e$; wherein, W that is $(C_{1-6})$hydrocarbylene is optionally substituted by 1, 2, or 3 substituents that are $OR^f$.

In some embodiments, X is $(C_{1-6})$hydrocarbylene, optionally substituted by 1, 2 or 3 substituents independently selected from halogen, $(C_{1-6})$alkyl, $(C_{1-4})$haloalkyl, CN and $OR^f$.

In some embodiments, X is selected from arylene, heteroarylene and heterocycloalkylene, each optionally substituted by 1, 2 or 3 substituents independently selected from halogen, $(C_{1-6})$alkyl, $(C_{1-4})$haloalkyl, CN and $OR^f$.

In some embodiments, X is arylene. In some embodiments, X is arylene selected from phenyl, naphthyl and anthryl. In some embodiments, X is phenylene.

In some embodiments, X is heteroarylene. In some embodiments, X is a five membered heteroarylene. In some embodiments, X is a five-membered heteroarylene wherein the heteroaryl ring is selected from pyrrole, furan, thiophene, imidazole, pyrazole, oxazole, isoxazole, thiazole, 1,2,3-triazole, 1,2,4-triazole, oxadiazole, and thiadiazole. In some embodiments, X is 1,2,4-oxadizole.

In some embodiments, Y is selected from $(C_{1-6})$hydrocarbylene, O, $SO_v$, $C(=O)$, $C(=O)NR^e$ and $SO_vNR^e$; wherein Y that is $(C_{1-6})$hydrocarbylene is optionally substituted by 1, 2 or 3 substituents independently selected from halogen and $OR^f$.

In some embodiments, Z is selected from H, halogen, CN, $OR^f$ and $(C_{1-14})$hydrocarbyl.

In some embodiments, Z is selected from $(C_{1-14})$hydrocarbyl, optionally substituted by 1, 2 or 3 substituents independently selected from halogen, $(C_{1-6})$hydrocarbyl, $(C_{1-4})$haloalkyl, CN and $OR^a$. In some embodiments, Z is aryl, optionally substituted by 1, 2 or 3 substituents independently selected from halogen, $(C_{1-6})$hydrocarbyl, $(C_{1-4})$haloalkyl, CN and $OR^a$. In some embodiments, Z is phenyl, optionally substituted by 1, 2 or 3 substituents independently selected from halogen, $(C_{1-6})$hydrocarbyl, $(C_{1-4})$haloalkyl, CN and $OR^a$.

In some embodiments, Z is selected from heteroaryl and heterocycloalkyl, optionally substituted by 1, 2 or 3 substituents independently selected from halogen, $(C_{1-6})$hydrocarbyl, $(C_{1-4})$haloalkyl, CN and $OR^a$.

In some embodiments, the compound has Formula II:

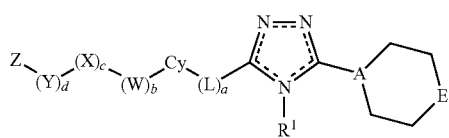

II

In some embodiments, the compound has Formula IIIa or IIIb:

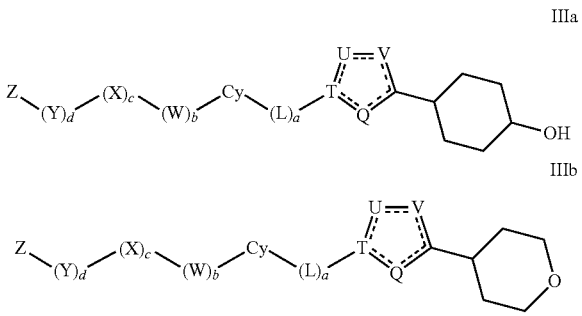

IIIa

IIIb

In some embodiments, the compound has Formula IVa or IVb:

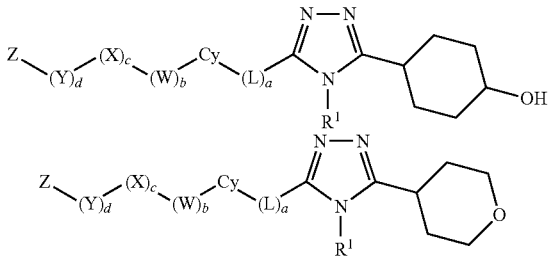

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

As used herein, the term "hydrocarbyl" refers to any moiety comprising only hydrogen and, carbon atoms, including but not limited to cycloalkyl, cycloalkylalkyl, aryl, arylalkyl, alkyl, alkenyl, alkynyl groups, and the like, and hydrocarbon groups that contain any combination of cycloalkyl, aryl, alkyl, alkenyl and alkynyl groups. Example hydrocarbyl groups include alkyl groups such as methyl, isopropyl and n-heptyl; alkenyl groups such as propenyl and 1,3-pentadienyl; alkynyl groups such as propargyl; aryl groups such as phenyl, naphthyl and anthryl; arylalkyl groups such as benzyl, phenethyl, mesityl and 2-phenylpropyl; cycloalkyl groups such cyclohexyl, norbornyl and cyclopropyl; and cycloalkylalkyl groups such as cyclopropylmethyl and cyclohexyl ethyl. Hydrocarbyl groups may be, for example, $(C_{1-20})$hydrocarbyl, $(C_{1-14})$hydrocarbyl, $(C_{1-10})$hydrocarbyl, $(C_{1-7})$hydrocarbyl. The term "hydrocarbylene" refers to a divalent hydrocarbyl group.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylene" refers to a divalent alkyl linking group.

As used herein, "alkenyl" refers to an alkyl group having one or more double carbon-carbon bonds. Example alkenyl groups include ethenyl, propenyl, cyclohexenyl, and the like. The term "alkenylene" refers to a divalent linking alkenyl group.

As used herein, "alkynyl" refers to an alkyl group having one or more triple carbon-carbon bonds. Example alkynyl groups include ethynyl, propynyl, and the like. The term "alkynylene" refers to a divalent linking alkynyl group.

As used herein, "haloalkyl" refers to an alkyl group having one or more halogen substituents. Example haloalkyl groups include $CF_3$, $CF_2Cl$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, and the like. In some embodiments, aryl groups have from 6 to about 20 carbon atoms. A linking aryl group is referred to herein as "arylene."

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) ring systems as well as spiro ring systems. Ring-forming carbon atoms of a cycloalkyl group can be optionally substituted by oxo or sulfido. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of pentane, pentene, hexane, and the like. Cycloalkyl groups containing a fused aromatic can be attached through either the aromatic or non-aromatic portion. A linking cycloalkyl group is referred to herein as "cycloalkylene."

As used herein, "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrrolyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms. A linking heteroaryl group is referred to herein as "heteroarylene."

As used herein, "heterocycloalkyl" refers to non-aromatic heterocycles where one or more of the ring-forming atoms is a heteroatom such as an O, N or S atom. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo or sulfido. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. Heterocycloalkyl groups containing a fused aromatic ring can be attached through either the aromatic or non-aromatic portion. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds. A linking heterocycloalkyl group is referred to herein as "heterocycloalkylene."

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "arylalkyl" refers to alkyl substituted by aryl and "cycloalkylalkyl" refers to alkyl substituted by cycloalkyl. An example arylalkyl group is benzyl.

As used herein, "heteroarylalkyl" refers to alkyl substituted by heteroaryl and "heterocycloalkylalkyl" refers to alkyl substituted by heterocycloalkyl.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a chromatographic column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

The term, "compound," as used herein is meant to include all stereoisomers, geometric iosomers, tautomers, and isotopes of the structures depicted.

All compounds, and pharmaceutically acceptable salts thereof, are also meant to include solvated or hydrated forms.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatograpy (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of the invention can be prepared, for example, using the reaction pathways and techniques as described below.

The preparation of compounds of formula I of the invention may be carried out in sequential or convergent synthetic routes. Syntheses of the invention are shown in the following schemes.

As shown in Scheme 1, a compound of Formula I, wherein U and V are N; T is C and Q is NR$^1$ (Formula I$^1$) can be synthesized by heating a mixture of 1-1 (a thioimidate when A is CH or a isothiourea when A is N) with acylhydrazide 1-2 in a suitable solvent in the presence of a suitable base such as sodium acetate when 1-2 is a salt. Suitable solvents include, for example, a mixture of dioxane and water. The product of Formula I$^1$ can be optionally further functionalized by routine methods to afford other compounds of Formula I.

Scheme 1

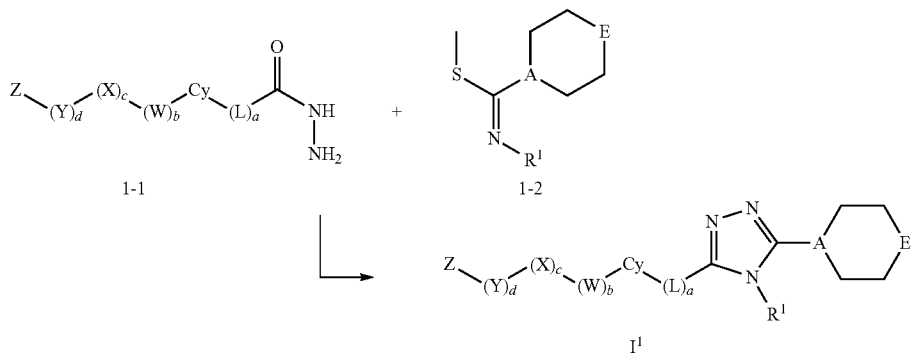

When A is N, a compound of Formula I¹ can also be prepared, as illustrated in Scheme 2, by reaction of iminoether 2-1 with acylhydrazide 2-2 in a boiling inert solvent, such as toluene, in the presence of a tertiary amine such as triethylamine.

Scheme 2

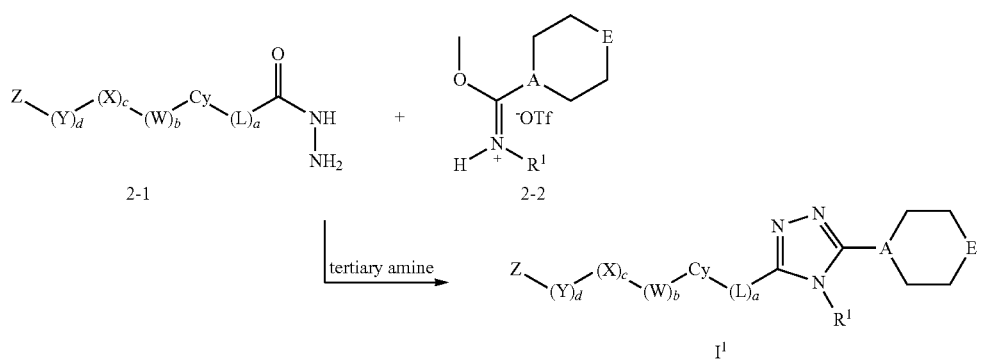

Alternatively, as shown in Scheme 3, a triazole compound of Formula I¹ wherein A is carbon can be prepared by treatment of a thioimidate or isothiourea 3-1 with an acylhydrazide 3-2 under conditions as described for Scheme 1.

Scheme 3

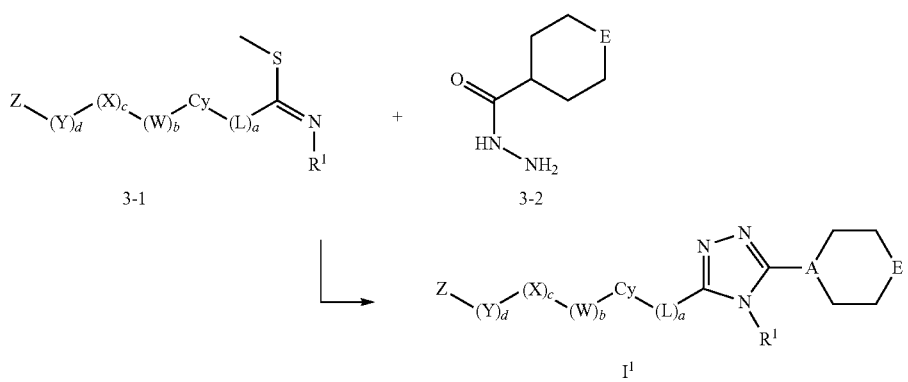

The thioimidate and isothiourea intermediates, such as 3-1 and 1-2, can be synthesized by known methods. For example, one preparation of thioimidate and isothiourea 1-2 is illustrated in Scheme 4 below. According to Scheme 4, an appropriately protected carboxylic acid 4-1 can be converted to corresponding amide 4-2 (wherein A is C) by direct coupling of the acid with an amine $R^1NH_2$ in the presence of a suitable coupling reagent such as 1-ethyl-3-(3-dimethylaminopropyl)-carbodiimide (EDC) or benzotriazol-1-yloxy-tris(dimethylamino)phosphonium hexafluoro-phosphate (BOP). Alternatively, the carboxylic acid 4-1 can be converted to corresponding acid chloride. The acid chloride can then be further treated with an amine $R^1NH_2$ in the presence of a base, such triethylamine or pyridine, to provide the amide 4-2. Treatment of 4-2 with Lawesson's reagent provides a thioamide 4-3 (wherein A is C). Alternatively, an amine 4-4 can be converted to a thiourea 4-3 (wherein A is N) by treating the amine 4-4 with isothiocyanate $R^1NCS$. Reaction of 4-3 with a methylating agent such as iodomethane, methyl trifluorosulfonate, or methyl sulfate in the absence or presence of a base yields 1-2 or its corresponding salt.

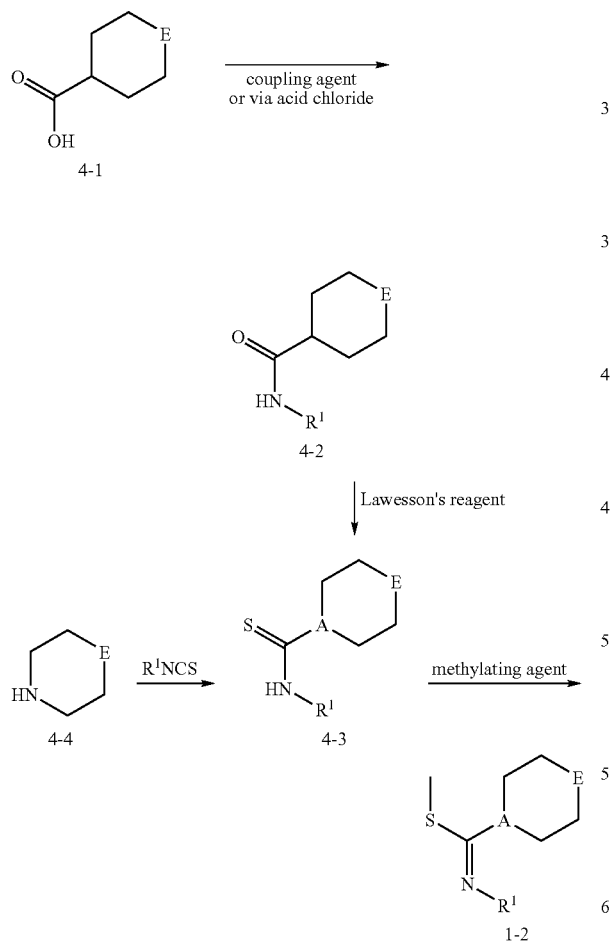

As shown in Scheme 5, iminoether 2-2 (wherein A is C) can be obtained by heating a secondary amide 5-1 (wherein A is C) with neat methyl triflate or another suitable methylating reagent, such as methyl iodide or methyl sulfate.

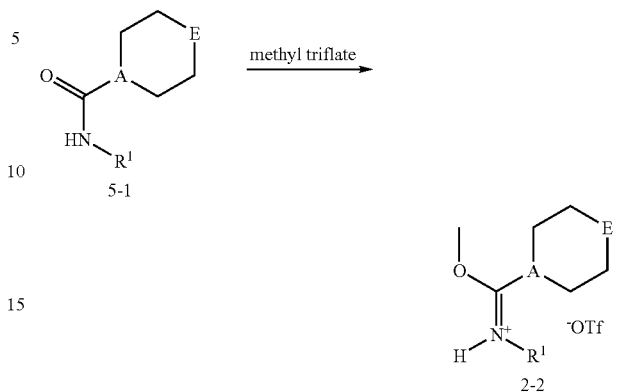

An acylhydrazide, such as 1-1 or 3-2, may be prepared by treating the corresponding carboxylic acid with a coupling agent such as, for example, N,N,N'N'-tetra-methylformamidinium hexafluorophoshpate, and hydrazine in the presence of a suitable base, such as triethylamine.

As illustrated in Scheme 6, the intermediate 1-1 may be prepared by treating the carboxylic acid 6-1 with a coupling reagent and hydrazine in the presence of a suitable base (e.g., triethylamine).

Alternatively, an acylhydrazide, such as 1-1 or 3-2, can be prepared by heating the corresponding carboxylic acid ester with hydrazine. As illustrated in Scheme 6, the acylhydrazide 1-1 may alternatively be prepared by treating the carboxylic acid ester 6-2 with hydrazine.

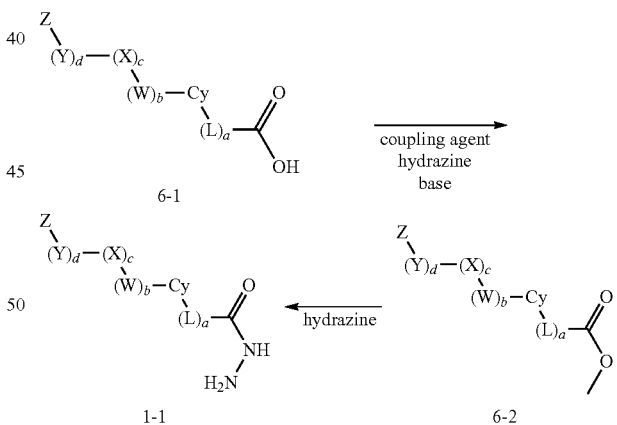

A carboxylic acid 7-3 (a compound of formula 6-1, wherein L is $CR^2R^3$, and $R^2$ and $R^3$ together with the carbon atom to which they are attached, form a cycloalkyl ring), can generally be prepared as shown in Scheme 7. According to Scheme 7, treatment of a nitrile compound 7-1 with a suitable dihalide (halo-$R^2$-$R^3$-halo) in the presence of a suitable base, such as potassium hydroxide, yields the nitrile compound 7-2. Hydrolysis of the nitrile functionality of compound 7-2 in the presence of a base, such as potassium hydroxide, in a boiling polar solvent, such as ethylene glycol, provides the carboxylic acid 7-3. The carboxylic acid 7-3 can be further derivatized to provide other carboxylic acids that can be incorporated into compounds of the invention.

Scheme 7

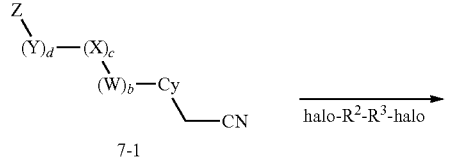

7-1

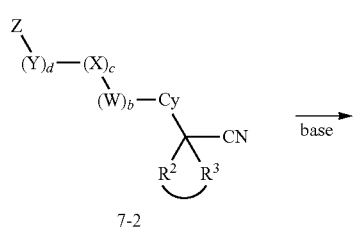

7-2

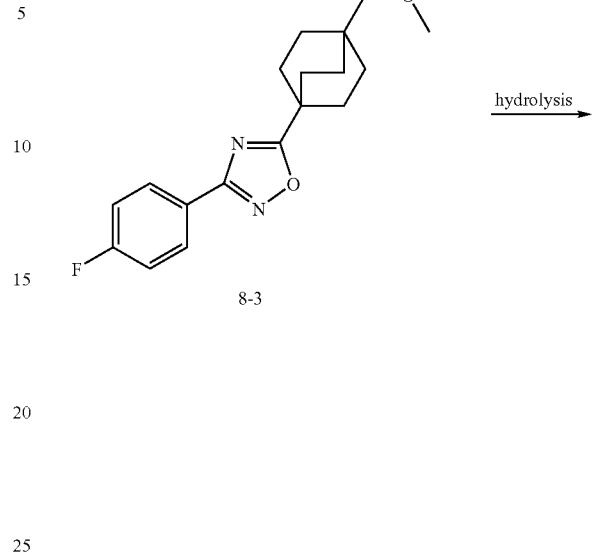

8-3

Provision of functional groups on compounds of Formula I can be achieved at various points in the syntheses of a compound of Formula I. Scheme 8 illustrates an example of installing functional groups at a point early in the synthesis. According to Scheme 8, a carboxylic acid 8-4 (a compound of formula 6-1, wherein a is 0, Cy is bicyclo[2,2,2]octanenyl) can be prepared by condensation of a bicyclo[2,2,2]octyl-1-carboxylic acid 8-1 with an amidoxime, such as compound 8-2 in the presence of a dehydrating agent, such as diisopropylcarbodiimide (DIC), or a peptide coupling reagent, such as carbonyldiimidazole (CDI), followed by hydrolysis of resulting ester 8-3.

Scheme 8

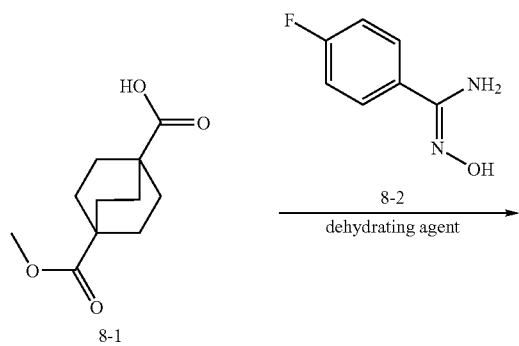

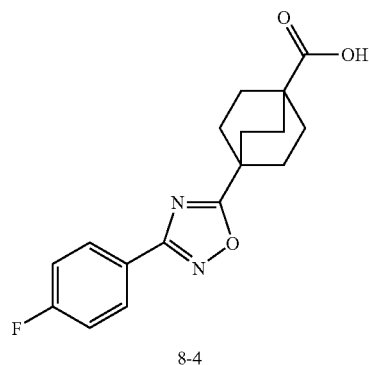

8-4

As shown in Scheme 9, a compound of Formula I, wherein U is N; V is O; T is C and Q is C—R$^1$ (Formula I$^2$) can be synthesized via a dipolar addition reaction between a nitrile oxide 9-1 and an alkyne compound 9-2 which can both be prepared by known methods. The product of Formula I$^2$ can be optionally further functionalized using known methods to afford other compounds of the invention.

Scheme 9

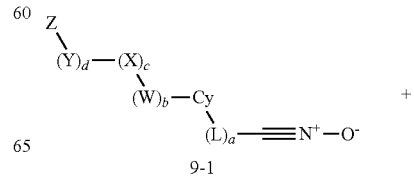

9-1

-continued

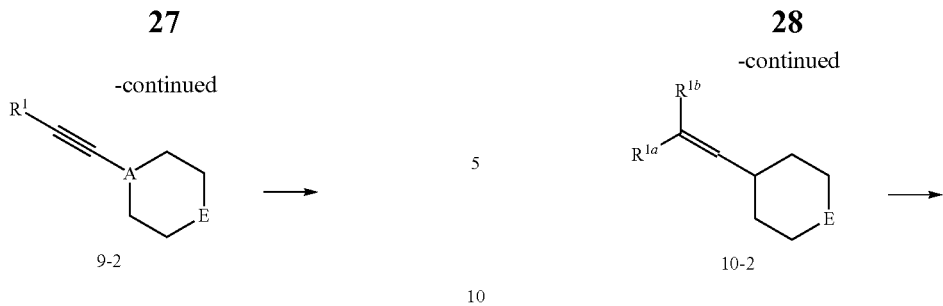

As shown in Scheme 10, a compound of Formula I, wherein U is N; V is O; T is C; Q is $C(R^{1a}R^{1b})$ and A is C (Formula $I^3$) can be synthesized via a dipolar addition reaction between a nitrile oxide 10-1 and an alkene compound 10-2, both of which can be prepared by known methods. The product of Formula $I^3$ can be optionally further functionalized using routine methods to afford other compounds of the invention.

Scheme 10

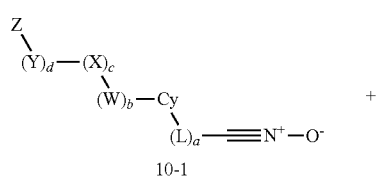

As shown in Scheme 11, a compound of Formula I, wherein U, V and T are N; Q is C—$R^1$ and A is C (Formula $I^4$) can be synthesized via a dipolar addition reaction between an azide 11-1 and an alkyne compound 11-2, both of which can be prepared by known methods. The product of Formula $I^4$ can be optionally further functionalized using known methods to afford other compounds of the invention.

Scheme 11

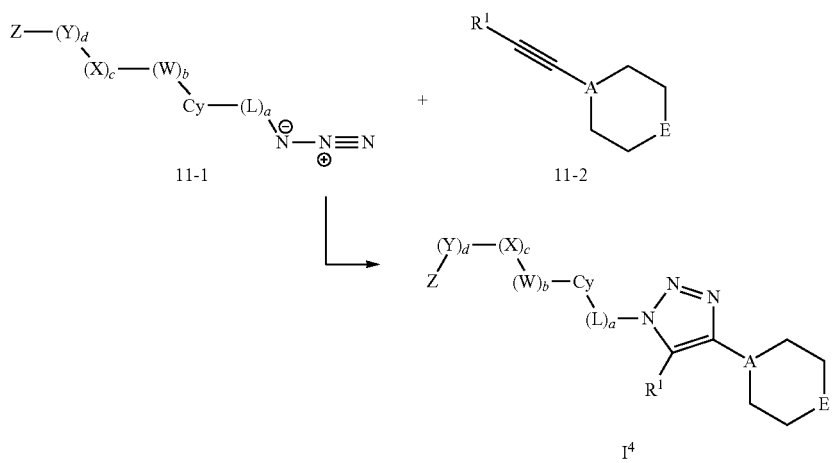

The nitrile oxide 10-1 may be obtained via known methods. For example, as shown in Scheme 12 an oxime 12-2 may be treated with N-chlorosuccinimide to provide a carboximidoyl chloride intermediate which may be subsequently reacted with a suitable base such as triethylamine to provide the nitrile oxide 10-1. As shown in Scheme 12, the oxime 12-2 may be prepared by reducing a carboxylic acid 6-1 to the corresponding aldehyde 12-1, and converting the aldehyde 12-1 to aldoxime 12-2 by reaction with hydroxylamine hydrochloride. The reduction of the carboxylic acid 6-1 to aldehyde 12-1 may be accomplished via known methods, for example, via reduction of the acid 6-1 to corresponding alcohol using a reducing reagent, such as borane-THF complex, followed by oxidation of the resulting alcohol with an oxidation agent, such as Jones reagent. The nitrile oxide 12-4, thus prepared is typically used in situ in the reaction with the dipolarphile 10-2 or 11-2 as shown in Schemes 10 and 11.

Scheme 12

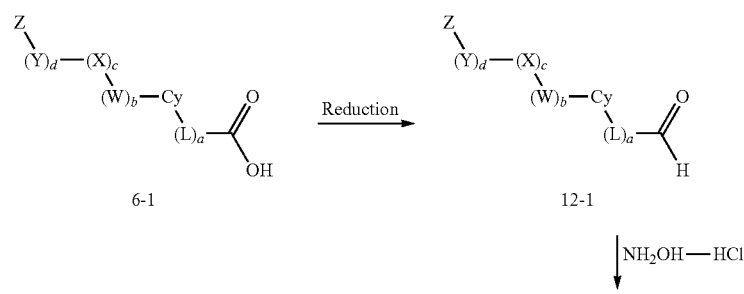

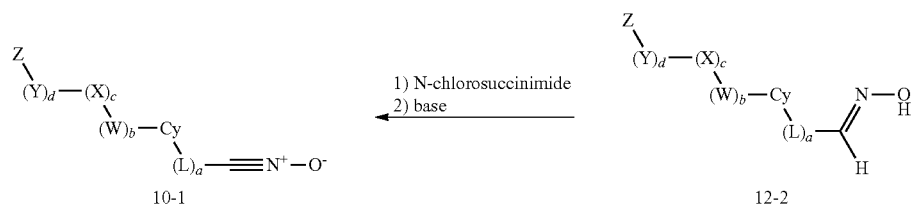

As shown in Scheme 13, a compound of Formula I, wherein U is O; V and Q are N; and T is C (Formula I⁵) can be synthesized by condensation of a carboxylic acid 6-1 with an amidoxime (13-1), which can be prepared by known methods, in the presence of a dehydration agent, e.g., DIC, or a peptide coupling reagent, e.g., CDI. The product of Formula I⁵ can be optionally further functionalized using routine methods to afford other compounds of the invention.

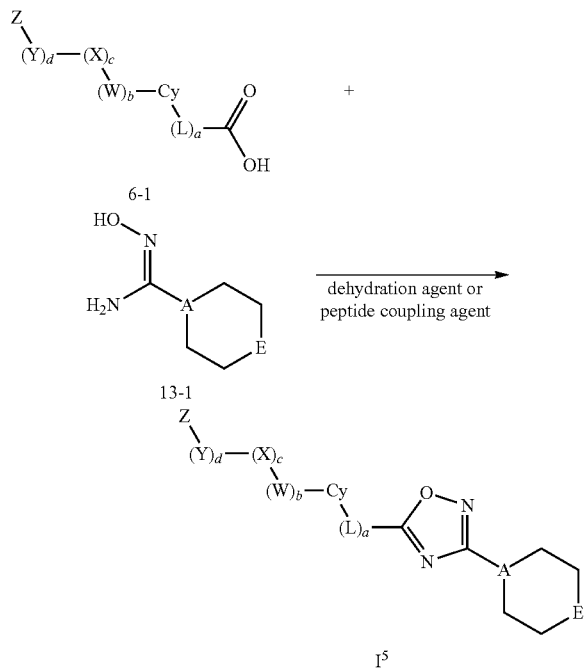

Scheme 13

As shown in Scheme 14, a compound of Formula I, wherein U and V are N or NR¹; Q is CR¹; and T is C (Formula I⁶) can be synthesized by condensation of a diketone 14-1, which can be prepared by known methods, with hydrazine. The product of Formula I⁶ can be optionally further functionalized using known methods to afford other compounds of the invention.

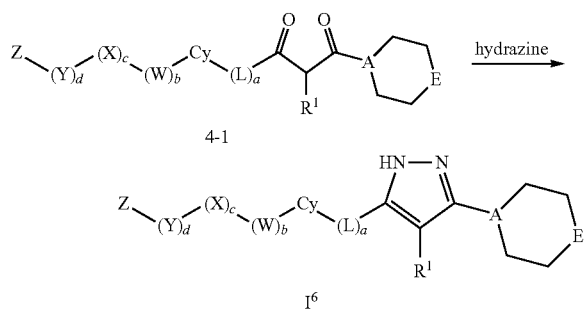

Scheme 14

Methods

Compounds of the invention can modulate activity of 11βHSD1. The term "modulate" is meant to refer to an ability to increase or decrease activity of an enzyme. Accordingly, compounds of the invention can be used in methods of modulating 11βHSD1 by contacting the enzyme with any one or more of the compounds or compositions described herein. In some embodiments, compounds of the present invention can act as inhibitors of 11βHSD1. In further embodiments, the compounds of the invention can be used to modulate activity of 11βHSD1 in an individual in need of modulation of the enzyme by administering a modulating amount of a compound of the invention.

The present invention further provides methods of inhibiting the conversion of cortisone to cortisol in a cell, or inhibiting the production of cortisol in a cell, where conversion to or production of cortisol is mediated, at least in part, by 11βHSD1 activity. Methods of measuring conversion rates of cortisone to cortisol and vice versa, as well as methods for measuring levels of cortisone and cortisol in cells, are routine in the art.

The present invention further provides methods of increasing insulin sensitivity of a cell by contacting the cell with a compound of the invention. Methods of measuring insulin sensitivity are routine in the art.

The present invention further provides methods of treating disease associated with activity or expression, including abnormal activity and overexpression, of 11βHSD1 in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the enzyme or receptor. An 11βHSD1-associated disease can also include any disease, disorder or condition that can be prevented, ameliorated, or cured by modulating enzyme activity.

Examples of 11βHSD1-associated diseases include obesity, diabetes, glucose intolerance, insulin resistance, hyperglycemia, atherosclerosis, hypertension, hyperlipidemia, cognitive impairment, dementia, depression (e.g., psychotic depression), glaucoma, cardiovascular disorders, osteoporosis, and inflammation. Further examples of 11βHSD1-associated diseases include metabolic syndrome, type 2 diabetes, androgen excess (hirsutism, menstrual irregularity, hyperandrogenism) and polycystic ovary syndrome (PCOS).

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal. In some embodiments, the cell is an adipocyte, a pancreatic cell, a hepatocyte, neuron, or cell comprising the eye.

As used herein, the term "contacting" refers to the bringing together of indicated moieties in an in vitro system or an in vivo system. For example, "contacting" the 11βHSD1 enzyme with a compound of the invention includes the administration of a compound of the present invention to an individual or patient, such as a human, having 11βHSD1, as well as, for example, introducing a compound of the invention into a sample containing a cellular or purified preparation containing the 11βHSD1 enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Pharmaceutical Formulations and Dosage Forms

When employed as pharmaceuticals, the compounds of Formula I can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, antibodies, immune suppressants, anti-inflammatory agents and the like.

Labeled Compounds and Assay Methods

Another aspect of the present invention relates to labeled compounds of the invention (radio-labeled, fluorescent-labeled, etc.) that would be useful not only in radio-imaging but also in assays, both in vitro and in vivo, for localizing and quantitating the enzyme in tissue samples, including human, and for identifying ligands by inhibition binding of a labeled compound. Accordingly, the present invention includes enzyme assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, 77Br, $^{123}$I, $^{124}$I, $^{125}$I and $^{131}$I. The radionuclide that is incorporated in the instant radio-labeled compounds will depend on the specific application of that radio-labeled compound. For example, for in vitro receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled compound" is a compound that has incorporated at least one radionuclide. In some embodiments the radionuclide is selected from the group consisting of $^3$H, $^{14}$C, $^{125}$I, $^{35}$S and $^{82}$Br.

In some embodiments, the labeled compounds of the present invention contain a fluorescent label.

Synthetic methods for incorporating radio-isotopes and fluorescent labels into organic compounds are well known in the art.

A labeled compound of the invention (radio-labeled, fluorescent-labeled, etc.) can be used in a screening assay to identify/evaluate compounds. For example, a newly synthesized or identified compound (i.e., test compound) which is labeled can be evaluated for its ability to bind a 11βHSD1 by monitoring its concentration variation when contacting with the 11βHSD1, through tracking the labeling. For another example, a test compound (labeled) can be evaluated for its ability to reduce binding of another compound which is known to bind to 11βHSD1 (i.e., standard compound). Accordingly, the ability of a test compound to compete with the standard compound for binding to the 11βHSD1 directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of 11βHSD1-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. The compounds of the Examples were found to inhibitors of 11βHSD1 according to one or more of the assays provided herein.

EXAMPLES

Example 1

4-{5-[1-(4-chlorophenyl)cyclopropyl]-4-methyl-4H-1,2,4-triazol-3-yl}cyclohexanol

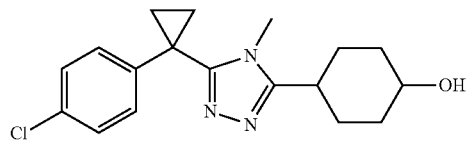

Step 1. 4-hydroxycyclohexanecarbohydrazide

A mixture of ethyl 4-hydroxycyclohexanecarboxylate (2.0 g, 12 mmol) and hydrazine (1.5 g, 46 mmol) in methanol (20 mL) was stirred at 55° C. for 4 h and then cooled to room temperature (about 25° C.). After cooling, the solvent and excess hydrazine were removed by distillation under reduced pressure to provide a residue. The residue was co-evaporated with methanol (2×), and was then dried under high vacuum to provide the crude product 4-hydroxycyclohexanecarbohydrazide, which was used in the next synthesis step without further purification. LCMS: $(M+H)^+=155.2$.

Step 2. 1-(4-chlorophenyl)cyclopropanecarbonyl chloride

A catalytic amount of N,N-dimethylformamide (DMF) (10 μL) was added to a mixture of 1-(4-chlorophenyl)cyclopropanecarboxylic acid (1.0 g, 5.1 mmol) and oxalyl chloride (2.2 mL, 25 mmol) in methylene chloride (5 mL) at 0° C. The resulting mixture was stirred at room temperature (about 25° C.) for 2 h. The volatiles were removed under reduced pressure, and the resulting residue was co-evaporated with toluene (2×) to provide the crude product, 1-(4-chlorophenyl)cyclopropanecarbonyl chloride, which was used in next step without further purification.

Step 3. 1-(4-chlorophenyl)-N-methylcyclopropanecarboxamide

A solution of methylamine in tetrahydrofuran (THF) (2.0 M, 3.5 mL) was mixed with triethylamine (2.1 mL, 15 mmol). The resulting mixture was added to a solution of 1-(4-chlorophenyl)cyclopropanecarbonyl chloride in methylene chloride (15.0 mL) at 0° C. The resulting mixture was stirred at room temperature (about 25° C.) for 30 min, and was then quenched with saturated sodium bicarbonate (25 mL). The quenched mixture was extracted with ethyl acetate (3×40 mL). The combined ethyl acetate extracts were washed with brine, dried over $Na_2SO_4$, and filtered. The filtrate was concentrated under reduced pressure to provide the product, 1-(4-chlorophenyl)-N-methylcyclopropanecarboxamide, which was used in next step without further purification.

Step 4. 4-{5-[1-(4-chlorophenyl)cyclopropyl]-4-methyl-4H-1,2,4-triazol-3-yl}cyclohexanol

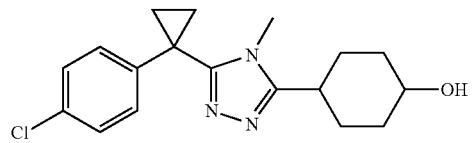

Methyl trifluoromethanesulfonate (53.9 μL, 0.491 mmol) was added to 1-(4-chlorophenyl)-N-methylcyclopropanecarboxamide (100.0 mg, 0.48 mmol). The resulting reaction mixture was stirred at 60° C. for 30 min. To the reaction mixture were then added toluene (2.0 mL), triethylamine (68.6 μL, 0.492 mmol) and 4-hydroxycyclohexanecarbohydrazide (38 mg, 0.24 mmol). The resulting mixture was stirred for 3 h at 60° C. and an additional 1 h. at 110° C. The mixture was then cooled to room temperature (about 25° C.). After cooling, the reaction mixture was concentrated to provide a residue. The residue was purified by Prep-HPLC to afford the desired products (cis- and trans-two isomers). Isomer I: LCMS: $(M+H)^+=332.2/334.2$; isomer II: LCMS: $(M+H)^+=332.1/334.1$.

Example 2

3-[1-(4-chlorophenyl)cyclopropyl]-4-methyl-5-(tetrahydro-2H-pyran-4-yl)-4H-1,2,4-triazole.

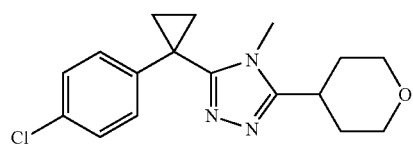

This compound was prepared using procedures analogous to those for Example 1. LCMS: $(M+H)^+=318.1/320.1$.

Example A

Enzymatic Assay of 11βHSD1

All in vitro assays were performed with clarified lysates as the source of 11βHSD1 activity. HEK-293 transient transfectants expressing an epitope-tagged version of full-length human 11βHSD1 were harvested by centrifugation. Roughly $2\times10^7$ cells were resuspended in 40 mL of lysis buffer (25 mM Tris-HCl, pH 7.5, 0.1 M NaCl, 1 mM $MgCl_2$ and 250 mM sucrose) and lysed in a microfluidizer. Lysates were clarified by centrifugation and the supernatants were aliquoted and frozen.

Inhibition of 11βHSD1 by test compounds was assessed in vitro by a Scintillation Proximity Assay (SPA). Dry test compounds were dissolved at 5 mM in DMSO. These were diluted in DMSO to suitable concentrations for the SPA assay. 0.8 μL of 2-fold serial dilutions of compounds were dotted on 384 well plates in DMSO such that 3 logs of compound concentration were covered. 20 μL of clarified lysate was added to each well. Reactions were initiated by addition of 20 μL of substrate-cofactor mix in assay buffer (25 mM Tris-HCl, pH 7.5, 0.1 M NaCl, 1 mM $MgCl_2$) to final concentrations of 400 μM NADPH, 25 nM $^3$H-cortisone and 0.007% Triton X-100. Plates were incubated at 37° C. for one hour. Reactions were quenched by addition of 40 μL of anti-mouse coated SPA beads that had been pre-incubated with 10 μM carbenoxolone and a cortisol-specific monoclonal antibody. Quenched plates were incubated for a minimum of 30 minutes at RT prior to reading on a Topcount scintillation counter. Controls with no lysate, inhibited lysate, and with no mAb were run routinely. Roughly 30% of input cortisone is reduced by 11βHSD1 in the uninhibited reaction under these conditions.

Test compounds having an $IC_{50}$ value less than about 20 μM according to this assay were considered active.

Example B

Cell-Based Assays for HSD Activity

Peripheral blood mononuclear cells (PBMCS) were isolated from normal human volunteers by Ficoll density centrifugation. Cells were plated at $4 \times 10^5$ cells/well in 200 μL of AIM V (Gibco-BRL) media in 96 well plates. The cells were stimulated overnight with 50 ng/ml recombinant human IL-4 (R&D Systems). The following morning, 200 nM cortisone (Sigma) was added in the presence or absence of various concentrations of compound. The cells were incubated for 48 hours and then supernatants were harvested. Conversion of cortisone to cortisol was determined by a commercially available ELISA (Assay Design).

Test compounds having an $IC_{50}$ value less than about 20 μM according to this assay were considered active.

A number of embodiments of the invention have been described. Nevertheless, it will be understood that various modifications may be made without departing from the spirit and scope of the invention. Accordingly, other embodiments are within the scope of the following claims. Each reference, including all patent, patent applications, and publications, cited in the present application is incorporated herein by reference in its entirety.

What is claimed is:
1. A compound of Formula I:

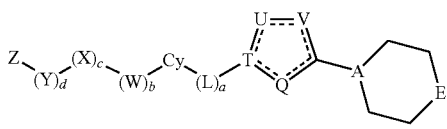

I or a pharmaceutically acceptable salt thereof, wherein:
A is CH;
E is O or $C(OR^{E1})R^{E2}$;
$R^{E1}$ and $R^{E2}$ are each H;
Q is N or $NR^1$;
T is C;
U is N or $NR^{1c}$;
V is N or $NR^{1e}$;
----- is a single or double bond;
$R^1$, $R^{1c}$ and $R^{1e}$ are independently selected from H, $(C_{1-6})$alkyl and $(C_{3-6})$cycloalkyl; wherein $R^{1c}$ or $R^{1e}$ that is $(C_{1-6})$alkyl or $(C_{3-6})$cycloalkyl is optionally substituted by 1, 2 or 3 substituents independently selected from halogen, $CF_3$, OH, $(C_{1-6})$alkoxy, $(C_{3-6})$cycloalkyl and heterocycloalkyl;
L is $(CR^2R^3)_m$ or $(CR^2R^3)_n$-J-$(CR^2R^3)_p$;
$R^2$ and $R^3$ are independently selected from H and $(C_{1-6})$alkyl; wherein $R^2$ and $R^3$ that are $(C_{1-6})$alkyl are optionally substituted by 1, 2 or 3 substituents independently selected from halogen, CN and $OR^4$;
or $R^2$ and $R^3$, together with the carbon atom to which they are attached, form a 3-, 4-, 5-, 6- or 7-membered cycloalkyl ring or a 3-, 4-, 5-, 6- or 7-membered heterocycloalkyl ring, each optionally substituted by 1, 2 or 3 substituents independently selected from halogen, CN and $OR^4$;
n, m and p are independently selected from 0, 1, 2, 3 and 4;
J is selected from O, $SO_v$, C(=O), $NR^4$, $NR^4C$(=O), $NR^4SO_2$, $NR^4C$(=O)$NR^4$, C(=O) and OC(=O);
v is 1 or 2;
$R^4$ is independently selected from H, $(C_{1-6})$alkyl, $(C_{3-6})$cycloalkyl and $(C_{3-6})$cycloalkyl$(C_{1-4})$alkyl;
Cy is arylene, heteroarylene, heterocycloalkylene, or cycloalkylene, each optionally substituted by 1, 2 or 3 substituents independently selected from halogen, $(C_{1-4})$alkyl, $(C_{2-4})$alkenyl, $(C_{2-4})$alkynyl, $(C_{1-4})$haloalkyl, CN, $NO_2$, $OR^a$, $SR^a$, C(=O)$OR^a$, $(O)_uC$(=O)$R^b$, $(O)_uC$(=O)$NR^cR^d$, $NR^cR^d$, $NR^cC$(=O)$R^b$, $NR^cC$(=O)$OR^a$, $SO_vR^b$, and $SO_vNR^cR^d$;
u is 0 or 1;
$R^a$ is independently selected from H, $(C_{1-10})$hydrocarbyl, C(=O)$(C_{1-10})$hydrocarbyl, $(C_{1-6})$haloalkyl, heteroaryl, heteroaryl$(C_{1-3})$alkyl, heterocycloalkyl, and heterocycloalkyl$(C_{1-3})$alkyl; wherein $R^a$ that is $(C_{1-10})$hydrocarbyl, $(C_{1-6})$haloalkyl, heteroaryl, heteroaryl$(C_{1-3})$alkyl, heterocycloalkyl, or heterocycloalkyl$(C_{1-3})$alkyl is optionally substituted with OH, $NH_2$, halogen, CN, $(C_{1-7})$hydrocarbyl, $(C_{1-6})$haloalkyl, $(C_{1-6})$alkoxy, heteroaryl, heteroaryl$(C_{1-3})$alkyl, heterocycloalkyl, or heterocyclo-alkyl $(C_{1-3})$alkyl;
$R^b$ is independently selected from H, $(C_{1-10})$hydrocarbyl, $(C_{1-6})$haloalkyl, heteroaryl, heteroaryl$(C_{1-3})$alkyl, heterocycloalkyl, and heterocycloalkyl$(C_{1-3})$alkyl; wherein $R^b$ that is $(C_{1-10})$hydrocarbyl, $(C_{1-6})$haloalkyl, heteroaryl, heteroaryl$(C_{1-3})$alkyl, heterocycloalkyl or heterocycloalkyl$(C_{1-3})$alkyl is optionally substituted with OH, $NH_2$, halogen, CN, $(C_{1-7})$hydrocarbyl, $(C_{1-6})$ haloalkyl, $(C_{1-6})$alkoxy, heteroaryl, heteroaryl$(C_{1-3})$ alkyl, heterocycloalkyl, or heterocycloalkyl$(C_{1-3})$alkyl;
$R^c$ and $R^d$ are independently selected from H, $(C_{1-10})$hydrocarbyl, $(C_{1-6})$haloalkyl, heteroaryl, heteroaryl$(C_{1-3})$ alkyl, heterocycloalkyl, and heterocycloalkyl$(C_{1-3})$ alkyl;
wherein $R^c$ and $R^d$ that are $(C_{1-10})$hydrocarbyl, $(C_{1-6})$haloalkyl, heteroaryl, heteroaryl$(C_{1-3})$alkyl, heterocycloalkyl, or heterocycloalkyl$(C_{1-3})$alkyl are optionally substituted with OH, $NH_2$, halogen, CN, $(C_{1-7})$hydrocarbyl, $(C_{1-6})$haloalkyl, $(C_{1-6})$alkoxy, heteroaryl, heteroaryl$(C_{1-3})$alkyl, heterocycloalkyl, or heterocycloalkyl$(C_{1-3})$alkyl;
or $R^c$ and $R^d$, together with the N atom to which they are attached, form a 4-, 5-, 6- or 7-membered heterocycloalkyl ring;
W is selected from $(C_{1-6})$hydrocarbylene, O, $SO_v$, $NR^e$, C(=O), C(=O)O, C(=O)$NR^e$, $SO_vNR^e$ and $NR^eC$(=O)$NR^e$; wherein W that is $(C_{1-6})$hydrocarbylene is optionally substituted by 1, 2 or 3 substituents independently selected from halogen, $OR^f$ and $NR^f_2$;

$R^e$ is independently selected from H, $(C_{1-10})$hydrocarbyl, $C(=O)(C_{1-10})$hydrocarbyl, $(C_{1-6})$haloalkyl, heteroaryl, heteroaryl$(C_{1-3})$alkyl, heterocycloalkyl, and heterocycloalkyl$(C_{1-3})$alkyl; wherein $R^e$ that is $(C_{1-10})$hydrocarbyl, $(C_{1-6})$haloalkyl, heteroaryl, heteroaryl$(C_{1-3})$alkyl, heterocycloalkyl, or heterocycloalkyl$(C_{1-3})$alkyl is optionally substituted with OH, $NH_2$, halogen, $(C_{1-7})$hydrocarbyl, $(C_{1-6})$haloalkyl, heteroaryl, heteroaryl$(C_{1-3})$alkyl, heterocycloalkyl, or heterocycloalkyl$(C_{1-3})$alkyl;

$R^f$ is independently selected from H, $(C_{1-4})$alkyl, and $(C_{1-4})$haloalkyl;

X is selected from $(C_{1-6})$hydrocarbylene, arylene, heteroarylene, and heterocycloalkylene; wherein X that is $(C_{1-6})$hydrocarbylene, arylene, heteroarylene, or heterocycloalkylene is optionally substituted by 1, 2 or 3 substituents independently selected from halogen, $(C_{1-6})$alkyl, $(C_{2-6})$alkenyl, $(C_{2-6})$alkynyl, $(C_{1-4})$haloalkyl, CN, $NO_2$, $OR^f$ and $NR^f_2$;

Y is selected from $(C_{1-6})$hydrocarbylene, O, $SO_v$, $NR^e$, $C(=O)$, $C(=O)O$, $C(=O)NR^e$, $SO_vNR^e$, or $NR^eC(=O)NR^e$; wherein Y that is $(C_{1-6})$hydrocarbylene is optionally substituted by 1, 2 or 3 substituents independently selected from halogen, $OR^f$, and $NR^f_2$;

Z is selected from H, halogen, CN, $NO_2$, $OR^f$, $NR^f_2$, $(C_{1-14})$hydrocarbyl, heteroaryl, and heterocycloalkyl; wherein Z that is $(C_{1-14})$hydrocarbyl, heterocycloalkyl, or heteroaryl is optionally substituted by 1, 2 or 3 substituents independently selected from halogen, $(C_{1-6})$hydrocarbyl, $(C_{1-4})$haloalkyl, aryl, heteroaryl, heterocycloalkyl, CN, $NO_2$, $OR^a$, $SR^a$, $(O)_uC(=O)R^b$, $(O)_uC(=O)NR^cR^d$, $(O)_uC(=O)(O)_uR^a$, $NR^cR^d$, $NR^cC(=O)R^b$, $NR^cC(=O)OR^a$, $NR^cSO_2R^b$, $SO_vR^b$ and $SO_vNR^cR^d$; and a, b, c and d are independently selected from 0 and 1;
provided that the compound of Formula I is other than 1-(4-methyl-5-(1-phenylcyclopropyl)-4H-1,2,4-triazol-3-yl)piperidin-4-ol; 4-(4-methyl-5-(1-phenylcyclopropyl)-4H-1,2,4-triazol-3-yl)morpholine; and 3-(1-adarnantyl)-4-methyl-5-(tetrahydro-2H-pyran-4-yl)-4H-1,2,4-triazole.

2. The compound of claim 1, or pharmaceutically acceptable salt thereof, wherein U and V are both N; T is C; and Q is $N-R^1$.

3. The compound of claim 1, or pharmaceutically acceptable salt thereof, wherein E is O.

4. The compound of claim 1, or pharmaceutically acceptable salt thereof, wherein E is $C(OR^{E1})R^{E2}$ and $R^{E1}$ and $R^{E2}$ are H.

5. The compound of claim 1, or pharmaceutically acceptable salt thereof, wherein Cy is arylene or cycloalkylene, each optionally substituted by 1, 2, or 3 substituents selected from halogen, $(C_{1-4})$alkyl, $(C_{1-4})$haloalkyl, CN and $OR^a$.

6. The compound of claim 5, or pharmaceutically acceptable salt thereof, wherein Cy is phenyl, optionally substituted with halogen.

7. The compound of claim 5, or pharmaceutically acceptable salt thereof, wherein Cy is bicycle[2.2.23]octanyl, optionally substituted by 1, 2 or 3 substituents selected from halogen, $(C_{1-4})$alkyl, $(C_{1-4})$haloalkyl, CN and $OR^a$.

8. A compound of Formula I:

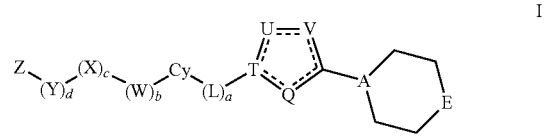

or pharmaceutically acceptable salt thereof, wherein:
A is CH;
E is O or $C(OR^{E1})R^{E2}$;
$R^{E1}$ and $R^{E2}$ are each H;
Q is N or $NR^1$;
T is C;
U is N or $NR^{1c}$;
V is N or $NR^{1e}$;
----- is a single or double bond;
$R^1$, $R^{1c}$ and $R^{1e}$ are independently selected from H, $(C_{1-6})$alkyl and $(C_{3-6})$cycloalkyl; wherein $R^1$, $R^{1c}$, or $R^{1e}$ that is $(C_{1-6})$alkyl or $(C_{3-6})$cycloalkyl is optionally substituted by 1, 2 or 3 substituents independently selected from halogen, $CF_3$, OH, $(C_{1-6})$alkoxy, $(C_{3-6})$cycloalkyl and heterocycloalkyl;
L is $(CR^2R^3)$;
$R^2$ and $R^3$ are independently selected from H and $(C_{1-6})$alkyl; wherein $R^2$ and $R^3$ that are $(C_{1-6})$alkyl are optionally substituted by 1, 2 or 3 substituents independently selected from halogen, CN and $OR^4$;
or $R^2$ and $R^3$, together with the carbon atom to which they are attached, form a 3-, 4-, 5-, 6- or 7-membered cycloalkyl ring or a 3-, 4-, 5-, 6- or 7-membered heterocycloalkyl ring, each optionally substituted by 1, 2 or 3 substituents independently selected from halogen, CN and $OR^4$;
n, m and p are independently selected from 0, 1, 2, 3 and 4;
J is selected from O, $SO_v$, $C(=O)$, $NR^4$, $NR^4C(=O)$, $NR^4SO_2$, $NR^4C(=O)NR^4$, $C(=O)O$ and $OC(=O)$;
v is 1 or 2;
$R^4$ is independently selected from H, $(C_{1-6})$alkyl, $(C_{3-6})$cycloalkyl, and $(C_{3-6})$cycloalkyl$(C_{1-4})$alkyl;
Cy is arylene, heteroarylene, heterocycloalkylene, or cycloalkylene, each optionally substituted by 1, 2 or 3 substituents independently selected from halogen, $(C_{1-4})$alkyl, $(C_{2-4})$alkenyl, $(C_{2-4})$alkynyl, $(C_{1-4})$haloalkyl, CN, $NO_2$, $OR^a$, $SR^a$, $C(=O)OR^a$, $(O)_uC(=O)R^b$, $(O)_uC(=O)NR^cR^d$, $NR^cR^d$, $NR^cC(=O)R^b$, $NR^cC(=O)OR^a$, $SO_vR^b$, and $SO_vNR^cR^d$;
u is 0 or 1;
$R^a$ is independently selected from H, $(C_{1-10})$hydrocarbyl, $C(=O)(C_{1-10})$hydrocarbyl, $(C_{1-6})$haloalkyl, heteroaryl, heteroaryl$(C_{1-3})$alkyl, heterocycloalkyl, and heterocycloalkyl$(C_{1-3})$alkyl; wherein $R^a$ that is $(C_{1-10})$hydrocarbyl, $(C_{1-6})$haloalkyl, heteroaryl, heteroaryl$(C_{1-3})$alkyl, heterocycloalkyl, or heterocycloalkyl$(C_{1-3})$alkyl is optionally substituted with OH, $NH_2$, halogen, CN, $(C_{1-7})$hydrocarbyl, $(C_{1-6})$haloalkyl, $(C_{1-6})$alkoxy, heteroaryl, heteroaryl$(C_{1-3})$alkyl, heterocycloalkyl, or heterocyclo-alkyl$(C_{1-3})$alkyl;
$R^b$ is independently selected from H, $(C_{1-10})$hydrocarbyl, $(C_{1-6})$haloalkyl, heteroaryl, heteroaryl$(C_{1-3})$alkyl, heterocycloalkyl, and heterocycloalkyl$(C_{1-3})$alkyl; wherein $R^b$ that is $(C_{1-10})$hydrocarbyl, $(C_{1-6})$haloalkyl, heteroaryl, heteroaryl$(C_{1-3})$alkyl, heterocycloalkyl or heterocycloalkyl$(C_{1-3})$alkyl is optionally substituted with OH, $NH_2$, halogen, CN, $(C_{1-7})$hydrocarbyl, $(C_{1-6})$ haloalkyl, $(C_{1-6})$alkoxy, heteroaryl, heteroaryl$(C_{1-3})$alkyl, heterocycloalkyl, or heterocycloalkyl$(C_{1-3})$alkyl;

$R^c$ and $R^d$ are independently selected from H, $(C_{1-10})$hydrocarbyl, $(C_{1-6})$haloalkyl, heteroaryl, heteroaryl$(C_{1-3})$alkyl, heterocycloalkyl, and heterocycloalkyl$(C_{1-3})$alkyl;

wherein $R^c$ and $R^d$ that are $(C_{1-10})$hydrocarbyl, $(C_{1-6})$haloalkyl, heteroaryl, heteroaryl$(C_{1-3})$alkyl, heterocycloalkyl, or heterocycloalkyl$(C_{1-3})$alkyl are optionally substituted with OH, $NH_2$, halogen, CN, $(C_{1-7})$hydrocarbyl, $(C_{1-6})$haloalkyl, $(C_{1-6})$alkoxy, heteroaryl, heteroaryl$(C_{1-3})$alkyl, heterocycloalkyl, or heterocycloalkyl$(C_{1-3})$alkyl;

or $R^c$ and $R^d$, together with the N atom to which they are attached, form a 4-, 5-, 6- or 7-membered heterocycloalkyl ring;

W is selected from $(C_{1-6})$hydrocarbylene, O, $SO_v$, $NR^e$, $C(=O)$, $C(=O)O$, $C(=O)NR^e$, $SO_vNR^e$ and $NR^eC(=O)NR^e$; wherein W that is $(C_{1-6})$hydrocarbylene is optionally substituted by 1, 2 or 3 substituents independently selected from halogen, $OR^f$ and $NR^f_2$;

$R^e$ is independently selected from H, $(C_{1-10})$hydrocarbyl, $C(=O)(C_{1-10})$hydrocarbyl, $(C_{1-6})$haloalkyl, heteroaryl, heteroaryl$(C_{1-3})$alkyl, heterocycloalkyl, or heterocycloalkyl$(C_{1-3})$alkyl; wherein $R^e$ that is $(C_{1-10})$hydrocarbyl, $(C_{1-6})$haloalkyl, heteroaryl, heteroaryl$(C_{1-3})$alkyl, heterocycloalkyl, or heterocycloalkyl$(C_{1-3})$alkyl is optionally substituted with OH, $NH_2$, halogen, $(C_{1-7})$hydrocarbyl, $(C_{1-6})$haloalkyl, heteroaryl, heteroaryl$(C_{1-3})$alkyl, heterocycloalkyl, or heterocycloalkyl$(C_{1-3})$alkyl;

$R^f$ is independently selected from H, $(C_{1-4})$alkyl, and $(C_{1-4})$haloalkyl;

X is selected from $(C_{1-6})$hydrocarbylene, arylene, heteroarylene, and heterocycloalkylene; wherein X that is $(C_{1-6})$hydrocarbylene, arylene, heteroarylene, or heterocycloalkylene is optionally substituted by 1, 2 or 3 substituents independently selected from halogen, $(C_{1-6})$alkyl, $(C_{2-6})$alkenyl, $(C_{2-6})$alkynyl, $(C_{1-4})$haloalkyl, CN, $NO_2$, $OR^f$ and $NR^f_2$;

Y is selected from $(C_{1-6})$hydrocarbylene, O, $SO_v$, $NR^e$, $C(=O)$, $C(=O)O$, $C(=O)NR^e$, $SO_vNR^e$, or $NR^eC(=O)NR^e$; wherein Y that is $(C_{1-6})$hydrocarbylene is optionally substituted by 1, 2 or 3 substituents independently selected from halogen, $OR^f$, and $NR^f_2$;

Z is selected from H, halogen, CN, $NO_2$, $OR^f$, $NR^f_2$, $(C_{1-14})$hydrocarbyl, heteroaryl, and heterocycloalkyl; wherein Z that is $(C_{1-14})$hydrocarbyl, heterocycloalkyl, or heteroaryl is optionally substituted by 1, 2 or 3 substituents independently selected from halogen, $(C_{1-6})$hydrocarbyl, $(C_{1-4})$haloalkyl, aryl, heteroaryl, heterocycloalkyl, CN, $NO_2$, $OR^a$, $SR^a$, $(O)_uC(=O)R^b$, $(O)_uC(=O)NR^cR^d$, $(O)_uC(=O)(O)_uR^a$, $NR^cR^d$, $NR^cC(=O)R^b$, $NR^cC(=O)OR^a$, $NR^cSO_2R^b$, $SO_vR^b$ and $SO_vNR^cR^d$; and a, b, c and d are independently selected from 0 and 1;

provided that the compound of Formula I is other than 1-(4-methyl-5-(1-phenylcyclopropyl)-4H-1,2,4-triazol-3-yl)piperidin-4-ol; 4-(4-methyl-5-(1-phenylcyclopropyl)-4H-1,2,4-triazol-3-yl)morpholine; and 3-(1-adamantyl)-4-methyl-5-(tetrahydro-2H-pyran-4-yl)-4H-1,2,4-triazole.

9. The compound of claim 8, or pharmaceutically acceptable salt thereof, wherein $R^2$ and $R^3$, together with the carbon atom to which they are attached, form a 3-, 4-, 5-, 6-, or 7-membered cycloalkyl ring optionally substituted by 1, 2, or 3 substituents independently selected from halogen and $OR^4$.

10. The compound of claim 9, or pharmaceutically acceptable salt thereof, wherein the cycloalkyl ring is optionally substituted by halogen.

11. The compound of claim 8, or pharmaceutically acceptable salt thereof, wherein $R^2$ and $R^3$, together with the carbon atom to which they are attached, form a 3- or 4-membered cycloalkyl ring optionally substituted by 1, 2, or 3 substituents independently selected from halogen and $OR^4$.

12. The compound of claim 11, or pharmaceutically acceptable salt thereof, wherein the cycloalkyl ring is optionally substituted by halogen.

13. The compound of claim 1, or pharmaceutically acceptable salt thereof, wherein b, c and d are all 0; and Z is selected from H, halogen, CN, $OR^f$, $(C_{1-14})$hydrocarbyl, heteroaryl and heterocycloalkyl; and wherein Z that is $(C_{1-14})$hydrocarbyl, heteroaryl or heterocycloalkyl is optionally substituted by 1, 2, or 3 substituents independently selected from halogen, $(C_{1-6})$hydrocarbyl, $(C_{1-4})$haloalkyl, aryl, heteroaryl, heterocycloalkyl, CN, $OR^a$, and $C(O)(NR^cR^d)$.

14. The compound of claim 13, or pharmaceutically acceptable salt thereof, wherein Z is H, halogen, CN or $(C_{1-14})$hydrocarbyl.

15. The compound of claim 13, or pharmaceutically acceptable salt thereof, wherein Z is heteroaryl or heterocycloalkyl, each optionally substituted by 1 or 2 substituents selected from halogen, $(C_{1-4})$haloalkyl, CN, $OR^a$ and $C(O)_{u(NR}{}^cR^d)$.

16. The compound of claim 1, or pharmaceutically acceptable salt thereof, wherein W is O; c and d are 0; Z is selected from $(C_{1-14})$hydrocarbyl, heteroaryl and heterocycloalkyl; wherein each $(C_{1-14})$hydrocarbyl, heteroaryl or heterocycloalkyl is optionally substituted by 1, 2, or 3 substituents independently selected from halogen, CN, $OR^a$ and $C(O)_u(NR^cR^d)$.

17. The compound of claim 16, or pharmaceutically acceptable salt thereof;

wherein a is 0.

18. The compound of claim 1, or pharmaceutically acceptable salt thereof; wherein W is selected from $(C_{1-6})$hydrocarbylene, O, $SO_v$, $C(=O)$, $C(=O)NR^e$, $SO_vNR^e$, or $NR^eC(=O)NR^e$; wherein, W that is $(C_{1-6})$hydrocarbylene is optionally substituted by 1, 2 or 3 substituents that are $OR^f$.

19. The compound of claim 1, or pharmaceutically acceptable salt thereof; wherein X is $(C_{1-6})$hydrocarbylene, optionally substituted by 1, 2 or 3 substituents independently selected from halogen, $(C_{1-6})$alkyl, $(C_{1-4})$haloalkyl, CN and $OR^f$.

20. The compound of claim 1, or pharmaceutically acceptable salt thereof, wherein X is selected from arylene, heteroarylene and heterocycloalkylene, each optionally substituted by 1, 2, or 3 substituents independently selected from halogen, $(C_{1-6})$alkyl, $(C_{1-4})$haloalkyl, CN and $OR^f$.

21. The compound of claim 20, or pharmaceutically acceptable salt thereof; wherein X is heteroarylene.

22. The compound of claim 21, or pharmaceutically acceptable salt thereof, wherein X is 1,2,4-oxadizolenyl.

23. The compound of claim 1, or pharmaceutically acceptable salt thereof, wherein Y is selected from $(C_{1-6})$hydrocarbylene, O, $SO_v$, $C(=O)$, $C(=O)NR^e$ and $SO_vNR^e$; wherein Y that is $(C_{1-6})$hydrocarbylene is optionally substituted by 1, 2 or 3 substituents independently selected from halogen and $OR^f$.

24. The compound of claim 1, or pharmaceutically acceptable salt thereof, wherein Z is selected from H, halogen, CN, $OR^f$ and $(C_{1-14})$hydrocarbyl.

25. The compound of claim 1, or pharmaceutically acceptable salt thereof, wherein Z is selected from $(C_{1-14})$hydrocarbyl, heteroaryl and heterocycloalkyl; each optionally substituted by 1, 2 or 3 substituents independently selected from halogen, $(C_{1-6})$hydrocarbyl, $(C_{1-4})$haloalkyl, CN and $OR^a$.

26. The compound of claim 25, or pharmaceutically acceptable salt thereof, wherein Z is aryl.

27. The compound of claim 26, or pharmaceutically acceptable salt thereof, wherein Z is phenyl.

28. The compound of claim 1, or pharmaceutically acceptable salt thereof, wherein b is 0.

29. The compound of claim 1, or pharmaceutically acceptable salt thereof, wherein d is 0.

30. The compound of claim 1, wherein $R^2$ and $R^3$, together with the carbon to which they are attached, form a cyclopropane ring;

Cy is phenyl optionally substituted with halogen;

b, c and d are 0; and

Z is selected from H, halogen, CN, $OR^f$ and $(C_{1-6})$hydrocarbyl.

31. The compound of claim 30, or pharmaceutically acceptable salt thereof, wherein Z is halogen.

32. The compound of claim 1, or pharmaceutically acceptable salt thereof, wherein $R^2$ and $R^3$, together with the carbon to which they are attached, form a cyclopropane ring;

Cy is phenyl optionally substituted with halogen;

b, c and d are 0; and

Z is heteroaryl or heterocyloalkyl optionally substituted by $C(=O)NR^cR^d$.

33. The compound of claim 32, or pharmaceutically acceptable salt thereof; wherein Z is pyridinyl optionally substituted by $C(=O)NR^cR^d$.

34. The compound of claim 32, or pharmaceutically acceptable salt thereof, wherein Z is pyrazolyl optionally substituted by $C(=O)NR^cR^d$.

35. The compound of claim 32, or pharmaceutically acceptable salt thereof, wherein Z is piperazinyl optionally substituted by $C(=O)OR^a$.

36. The compound of claim 1, or pharmaceutically acceptable salt thereof, wherein $R^2$ and $R^3$, together with the carbon to which they are attached, form a cyclopropane ring;

Cy is phenyl optionally substituted with halogen;

W is O;

c and d are 0; and

Z is heteroaryl optionally substituted by halogen, CN, $OR^a$, $SR^a$, $(C_{1-6})$hydrocarbyl or $(C_{1-4})$haloalkyl.

37. The compound of claim 1, or pharmaceutically acceptable salt thereof, wherein a is 0;

Cy is bicyclo[2.2.2] octanyl;

b is 0;

X is heteroaryl;

d is 0; and

Z is aryl optionally substituted by halogen, CN, $OR^a$, $SR^a$, $(C_{1-6})$hydrocarbyl or $(C_{1-4})$haloalkyl.

38. The compound of claim 37, or pharmaceutically acceptable salt thereof, wherein X is 1,2,4-oxadiazolyl and Z is phenyl optionally substituted by halogen, CN, $OR^a$, $SR^a$, $(C_{1-6})$hydrocarbyl, or $(C_{1-4})$haloalkyl.

39. A compound selected from:
4-{5-[1-(4-chlorophenyl)cyclopropyl]-4-methyl-4H-1,2,4-triazol-3-yl} cyclohexanol; and
3-[1-(4-chlorophenyl)cyclopropyl]-4-methyl-5-(tetrahydro-2H-pyran-4-yl)-4H-1,2,4-triazole; and pharmaceutically acceptable salts thereof.

40. A composition comprising at least one compound of claim 1, or pharmaceutically acceptable salt thereof, and at least one pharmaceutically acceptable carrier.

41. A method of modulating activity of 11βHSD1 comprising contacting said 11βHSD1 with a compound of claim 1, or pharmaceutically acceptable salt thereof.

42. The method of claim 41, wherein said modulating is inhibiting.

43. A method of treating a disease in a patient, wherein said disease is associated with expression or activity of 11βHSD1 and is obesity, diabetes, glucose intolerance, insulin resistance, hyperglycemia, hypertension, hyperlipidemia, cognitive impairment, dementia, depression, glaucoma, cardiovascular disorders, osteoporosis, inflammation, metabolic syndrome, atherosclerosis, type 2 diabetes, androgen excess, or polycystic ovary syndrome (PCOS), comprising administering to said patient a therapeutically effective amount of a compound of claim 1, or pharmaceutically acceptable salt thereof.

44. A method of treating obesity, diabetes, glucose intolerance, insulin resistance, hyperglycemia, hypertension, hyperlipidemia, cognitive impairment, dementia, depression, glaucoma, cardiovascular disorders, osteoporosis, inflammation, metabolic syndrome, atherosclerosis, type 2 diabetes, androgen excess, or polycystic ovary syndrome (PCOS) in a patient, comprising administering to said patient a therapeutically acceptable amount of a compound of claim 1, or pharmaceutically acceptable salt thereof.

45. The compound of claim 8, or pharmaceutically acceptable salt thereof, wherein U and V are both N; T is C; and Q is N—$R^1$.

* * * * *

UNITED STATES PATENT AND TRADEMARK OFFICE
CERTIFICATE OF CORRECTION

PATENT NO. : 7,838,544 B2
APPLICATION NO. : 11/803808
DATED : November 23, 2010
INVENTOR(S) : Yun-Long Li, Jincong Zhuo and Wenqing Yao It is certified that error appears in the above-identified patent and that said Letters Patent is hereby corrected as shown below:

In the Claims

Col. 40, Line 17, Claim 1, delete "C(=O)" and insert -- C(=O)O --.

Col. 40, Lines 38-39 (approx.), Claim 1, delete "heterocyclo-alkyl" and insert -- heterocycloalkyl --.

Col. 41, Line 65, Claim 7, delete "bicycle[2.2.23]" and insert -- bicyclo[2.2.2] --.

Col. 42, Line 26, Claim 8, delete "(CR$^2$R$^3$" and insert -- CR$^2$R$^3$ --.

Col. 42, Lines 59-60, Claim 8, delete "heterocyclo-alkyl" and insert -- heterocycloalkyl --.

Col. 44, Line 28 (approx.), Claim 15, delete "C(O)$_{u(NR}$$^c$R$^d$)" and insert -- C(O)$_u$(NR$^c$R$^d$) --.

Col. 44, Line 37 (approx.), Claim 17, delete "thereof;" and insert -- thereof, --.

Col. 44, Line 41, Claim 18, delete "thereof;" and insert -- thereof, --.

Col. 44, Line 46, Claim 19, delete "thereof;" and insert -- thereof, --.

Col. 44, Line 56, Claim 21, delete "thereof;" and insert -- thereof, --.

Col. 45, Line 32 (approx.), Claim 32, delete "heterocyloalkyl" and insert -- heterocycloalkyl --.

Signed and Sealed this
Twenty-eighth Day of May, 2013

Teresa Stanek Rea
*Acting Director of the United States Patent and Trademark Office*